US006107059A

United States Patent [19]
Hart

[11] Patent Number: 6,107,059
[45] Date of Patent: Aug. 22, 2000

[54] PEPTIDE LIBRARY AND SCREENING METHOD

[75] Inventor: Charles P. Hart, Mountain View, Calif.

[73] Assignee: Affymax Technologies N.V., Curaco, Netherlands

[21] Appl. No.: 07/876,288

[22] Filed: Apr. 29, 1992

[51] Int. Cl.$^7$ ..................................................... C12P 21/04
[52] U.S. Cl. ........................ 435/69.7; 435/69.1; 435/69.8
[58] Field of Search ........................ 435/6, 7.1, 7.2–7.37, 435/7.8, 69.1, 69.7, 69.8

[56] References Cited

FOREIGN PATENT DOCUMENTS

| 0488170 | 6/1992 | European Pat. Off. . |
| 9014431 | 5/1989 | WIPO . |
| 9111454 | 1/1990 | WIPO . |

OTHER PUBLICATIONS

Plückthun and Ge, 1991, Angew. Chem. Int. Ed. Engl. 30:296–298.
Tuerk and Gold, 1990, Science 249:505–510.
Ellington and Szostak, 1990, Nature 346:818–822.
Bock et al., 1992, Nature 355:564–566.
Ellington and Szostak, 1992, Nature 355:850–852.
Scott and Smith, 1990, Science 249:386–390.
Devlin et al., 1990, Science 249:404–406.
Greenwood et al., 1991, J. Mol. Biol. 220:821–827.
Cwirla et al., 1990, Proc. Natl. Acad. Sci. USA 87:6387–6382.
di Guan et al., 1988, Gene 67: 21–30.
Maina et al., 1988, Gene 74: 365–373.
Bedouelle and Duplay, 1988, Eur. J. Biochem. 171: 541–549.
Sano and Cantor, 1991, BBRC 176:571–577.
Hochuli et al., Nov. 1988, Biotechnology, pp. 13221–1325.
Yoo et al., 1989, J. Biol. Chem. 264: 17078–17083.
Ong et al., 1989, Biotechnology 7: 604–607.
Smith and Johnson, 1988, Gene 67: 31–40.
Field and Song, 1989, Nature 340 (6230):245–246.
O'Neil et al., 1990, Science 249: 774–778.
Talanian et al., 1990, Science 249: 769–771.
Miller et al., 1985, EMBO J. 4: 1609–1614.
Brown and Argos, 1986, Nature 324: 215.
Parraga et al., 1990, Proc. Natl. Acad. Sci. USA 87: 137–141.
Berg et al., 1990, J. Biol. Chem. 265: 6513–6516.
Berg, 1989, Cell 57: 1065–1068.
Opipari et al., 1990, J. Biol. Chem. 265: 14705–14708.
Tagawa et al., 1990, J. Biol. Chem. 265: 20021–20026.
Olivera et al., 1990, Science 249: 257–263.
Young and Davis, 1983, Science 222: 778–782.
Schiff et al., Jun. 1988, Proc. Natl. Acad. Sci. USA 85:4195–4199.
Makowski et al., 1991, Biol. Trace Elem. Res. 29:93–109.
Valle et al., 1991, Proc. Natl. Acad. Sci. USA 88:999–1003.
Miller et al., Mar. 1992, Proc. Natl. Acad. Sci. USA 89:2032–2035.
Thukral et al., 1989, Molec. Cell. Biol. 9 (6): 2360–2369.
Nagai and Thøgersen, 1987, Meth. in Enzymology 153: 461–481.
Frankel et al., Proc. Natl. Acad. Sci. USA,1987, 84: 4841–4845.
Blumberg et al., Jul. 1987, Nature 328: 443–445.
Gibson et al., 1988, Protein Eng., 2 (3): 209–218.
Nagai et al., Mar. 1988, Nature 332: 284–286.
Parraga et al., Sep. 1988, Science 241: 1489–1492.
Scholtissek and Grosse, 1988, Gene 62: 55–64.
Danielsen et al., Jun. 1989, Cell 57: 1131–1138.
Lee et al., Aug. 1989, Science 245: 635–637.
Abath and Simpson, 1990, Peptide Res. 3 (4): 167–168.
Klevit et al., 1990, Proteins: Structure, Function, and Genetics 7: 215–226.
Regan and Clarke, 1990, Biochem. 29: 10878–10883.
Uhlén and Moks, 1990, Meth. in Enzymology 185: 129–143.
Kochoyan et al., Oct. 1991 Proc. Natl. Acad. Sci. USA 88: 8455–8459.
Kochoyan et al., 1991, Biochem. 30: 9396–9402.
Nardelli et al., Jan. 10, 1991, Nature 349: 175–178.
Sakaguchi et al., Apr. 15, 1991, J. Biol. Chem. 266(11): 7306–7311.
Thukral et al., Oct. 1991, Proc. Natl. Acad. Sci. USA 88: 9188–9192.
Todd et al., 1991, Proteins: Sructure, Function, and Genetics 10: 156–161.
Weiss et al., 1991, J. Am. Chem. Soc. 113: 6704–6706.
Desjarlais and Berg, 1992, Proteins: Structure, Function, and Genetics 12: 101–104.
Arkin and Youvan, Mar 1992, Bio/Tech. 10: 297–300.
Hooft van Huijsduijnen et al., 1992, Nucl. Acid. Res. 20 (4): 919.
Dasmahapatra et al., May 1992, Proc. Natl. Acad. Sci. USA 89: 4159–4162.
Maniatis et al. 1982. in Molecular Cloning A Laboratory Manual. Cold Spring Harbor Labs, N.Y.
Oliphant et al. 1986. Gene 177–183.

*Primary Examiner*—Bruce R. Campell
*Attorney, Agent, or Firm*—Townsend & Townsend & Crew

[57] ABSTRACT

A random peptide library constructed by transforming host cells with a collection of recombinant vectors that encode a fusion protein comprised of a carrier protein fused to a random peptide through a proteolytic cleavage site can be used to identify ligands that bind to a receptor. The screening method results in the formation of a complex comprising the fusion protein bound to a receptor through the random peptide ligand, and the random peptide can easily be identified and analyzed by virtue of the carrier protein and associated proteolytic cleavage site.

8 Claims, 12 Drawing Sheets

Cleavable C-terminal peptide fusion vector

```
wt   TACGGTGGTTTCCTGCGTCGTCAGTTCAAAGTTGTTACC

-3   A T A         AG      GC        C     G

-4     G G      G   A  ATG     C  G AC  A

-B   T AAGA C     G CA    CA G       C C    G

-C     AA C  C  G A  T  T  C   AT          A

-D      C   G C AA    T       G   T  TC    G

-2        G  A A  C    A  G          AA

-3   T TTA    C A T AA    T    CAT TTGG GGT

-5   G   C  G  A  AG AT  T  G    TGAGG    G A

-6 G        G   A A GA A C   TT       TC   T

37   T C  C  G           G G GTT    C    CTT

38   G       C   T       GACAA C       CC  A

39     C  G  GTA A       C                GG

40 A G           ACT  G   G    ACGTA  TG GGG

41     AC G  G  GTA     G GT      G   G A

42 C T C    A CA      G      T CT  G GG      T

76 GTG        G     A CT    TA ATC  C   A CG
```

FIGURE 5

| | | | | | | | | | | | | |
|---|---|---|---|---|---|---|---|---|---|---|---|---|
| wt | Y | G | G | F | L | R | R | Q | F | K | V | V | T |
| -3 | N | D | | | G | | R | | | A | | A | |
| -4 | # | | | L | | S | M | | S | R | T | D | |
| -B | F | K | S | | R | H | | K | | A | L | S | |
| -C | # | S | R | L | Q | L | L | P | L | # | | | |
| -D | | A | | S | K | | C | | | E | F | S | |
| -2 | | | | Y | P | | S | E | | | | N | |
| -3 | F | L | | S | I | Q | | # | S | Y | W | G | S |
| -5 | C | | | L | L | G | C | # | V | M | R | | A |
| -6 | D | | | V | Q | | | P | | # | | S | I |
| 37 | | | | L | | | | | R | V | L | | L |
| 38 | # | | | S | | | | | R | Q | T | | P |
| 39 | | A | | L | # | S | | H | | | | | R |
| 40 | K | | | | H | C | G | R | L | R | I | C | G |
| 41 | # | R | | L | # | | G | # | | E | G | I | |
| 42 | H | A | | S | | | | H | S | | G | | |
| 76 | V | | | C | | S | C | H | I | S | L | I | A |

PEPTIDE LIBRARY AND SCREENING METHOD

BACKGROUND OF THE INVENTION

1. Field of the Invention

The present invention relates generally to methods for selecting peptide ligands to receptor molecules of interest and for generating and screening large peptide libraries for peptides with desired binding characteristics. The invention also provides methods for optimizing a peptide ligand for improved binding to a receptor and for producing peptide ligands in purified form. The invention therefore relates generally to the field of molecular biology and has application in the field of pharmacology.

2. Description of Related Art

The isolation of ligands that bind biological receptors facilitates the discovery of useful compounds and processes. The ability to synthesize DNA chemically has aided the construction of extremely large collections of nucleic acid and peptide sequences as potential ligands. Recently developed methods allow efficient screening of libraries of biological polymers for desired binding activities (see Pl uckthun and Ge, 1991, *Angew. Chem. Int. Ed. Enql.* 30:296–298). For example, Tuerk and Gold, 1990, *Science* 249:505–510, report the isolation of RNA molecules with the ability to bind a particular protein and Ellington and Szostak, 1990, *Nature* 346:818–822, report the isolation of RNA molecules with the ability to bind a dye by alternate rounds of affinity selection and PCR amplification. Thiesen and Bach, 1990, *Nucl. Acids Res.* 18:3203–3209, used a similar technique to find double-stranded DNA sequences that bind a human transcription factor, while Bock et al., 1992, *Nature* 355:564–567, and Ellington and Szostak, 1992, *Nature* 355:850–852, utilized single-stranded DNA libraries.

Efficient peptide screening techniques often utilize physical or logical connections between each peptide and the nucleic acid that encodes each peptide. After rounds of affinity enrichment, such a connection allows identification, usually by amplification and sequencing, of the genetic material encoding interesting peptides. Several phage based systems for screening proteins and polypeptides have been described. The fusion phage approach of Parmley and Smith, 1988, *Gene* 73:305–318, can be used to screen proteins. Others have described phage based systems in which a peptide is fused to the coat protein of a filamentous phage (see U.S. Pat. No. 5,427,908, filed May 1, 1990; and U.S. Pat. No. 5,723,286, filed Jun. 20, 1990, which is a continuation-in-part of U.S. Pat. No. 5,432,018, filed Jun. 20, 1991, each of which is incorporated herein by reference; see also Scott and Smith, 1990, *Science* 249:386–390; Devlin et al., 1990, *Science* 249:404–406; Greenwood et al., 1991, *J. Mol. Biol.* 220:821–827 and Cwirla et al., 1990, *Proc. Natl. Acad. Sci. USA* 87:6378–6382; each of which is incorporated herein by reference).

In the latter publications, the authors describe expression of a peptide at the amino terminus of or internal to the pIII or pVIII protein of a filamentous phage. The connection between a peptide and the genetic material that encodes the peptide is established, because the fusion protein is part of the capsid enclosing the phage genomic DNA. Phage encoding peptide ligands for receptors of interest can be isolated from libraries of greater than $10^8$ peptides after several rounds of affinity enrichment followed by phage growth. In another random peptide display system, the random peptide library is constructed so that the peptide is expressed as a fusion product with a DNA binding protein (see U.S. Pat. No. 5,270,170, filed Oct. 16, 1991, incorporated herein by reference). The peptide library is constructed so that the DNA binding protein can bind to the recombinant DNA expression vector that encodes the fusion product that contains the peptide of interest.

There remains a need not only for methods of constructing peptide libraries in addition to the methods described above but also for random peptide presentation systems more particularly suited to the optimization of a lead peptide compound. There also remains a need for improved methods and reagents for presenting diverse ligands to a receptor, which methods and reagents force conformational restrictions onto the peptides presented.

The present invention provides random peptide libraries, methods for generating and screening those libraries, and associated reagents with significant advantages over the prior art methods.

SUMMARY OF THE INVENTION

The present invention provides random peptide libraries and methods for generating and screening those libraries to identify peptides that bind to receptor molecules of interest. The peptides are produced from libraries of random peptide expression vectors that encode peptides attached to a carrier protein. The invention provides large libraries of peptides for screening with a receptor to identify peptides that bind to the receptor. Using the present methods, one can identify a peptide as having a desired binding affinity for a molecule and then produce that peptide in analytical or preparative amounts. The peptides can be used for therapeutic, diagnostic, and related purposes, e.g., to bind a receptor and so inhibit or promote the activity of the receptor.

By identifying the peptide de novo, one need not know the sequence or structure of the receptor molecule or the sequence or structure of the natural binding partner of the receptor. Indeed, for many receptors, a binding partner has not yet been identified. A significant advantage of the present invention is that no prior information regarding an expected ligand structure is required to isolate peptide ligands of interest. The peptide identified will have biological activity, which is meant to include at least specific binding affinity for a selected receptor molecule and, in some instances, will further include the ability to block the binding of other compounds to the receptor, to stimulate or inhibit metabolic pathways, to act as a signal or messenger, to stimulate or inhibit cellular activity, and the like.

The number of possible receptor molecules for which peptide ligands may be identified by means of the present invention is virtually unlimited. For example, the receptor molecule may be an antibody (or a binding portion thereof). The antigen to which the antibody binds may be known and perhaps even sequenced, in which case the invention may be used to map epitopes of the antigen. If the antigen is unknown, such as with antigens involved in certain autoimmune diseases, for example, sera or other fluids from patients with the disease can be used in the present screening method to identify peptides, and consequently the antigen, that elicits the autoimmune response. One can also use the present screening method to tailor a peptide to a particular purpose. Once a peptide has been identified, that peptide can serve as, or provide the basis for, the development of a vaccine, a therapeutic agent, a diagnostic reagent, or other useful compounds.

The present invention can be used to identify peptide ligands for a wide variety of receptors in addition to antibodies. These include, by way of example and not limitation, growth factors, hormones, enzymes, interferons, interleukins, intracellular and intercellular messengers, lectins, cellular adhesion molecules, and the like, as well as the ligands for the corresponding receptors of the aforementioned molecules. Peptide ligands can also be identified by the methods of the present invention for molecules that are not peptides or proteins, e.g., carbohydrates, nucleic acids (DNA or RNA), non-protein organic compounds, metals, etc. Thus, although antibodies are widely available and conveniently manipulated, antibodies are merely representative of receptor molecules for which peptide ligands can be identified by means of the present invention.

The method of generating the peptide library of the invention comprises the steps of (a) transforming host cells with a set of recombinant DNA vectors that code for the expression of a tripartite fusion protein consisting essentially of a carrier protein, a peptide, and a proteolytic cleavage site between said carrier protein and said peptide, such that at least 1000 different transformants are formed, and each different transformant can express a tripartite fusion protein distinct from the fusion protein that can be expressed by the other different transformants; and (b) culturing said host cells transformed in step (a) under conditions suitable for expression of the fusion protein.

The screening and ligand isolation method of the invention comprises the steps of (a) placing the transformed host cells of the peptide library on a surface such that each different transformant is located on said surface at a location different from the location of the other different transformants; (b) rendering the fusion proteins present in said transformed host cells on said surface prepared in step (a) accessible for receptor binding by osmotic shock or lysis of said transformed host cells; (c) contacting the fusion proteins rendered accessible in step (b) with a labelled receptor under conditions conducive to specific peptide-receptor binding; and (d) identifying transformants that produce fusion proteins with peptides that bind to the receptor by virtue of the location of said labeled receptor on said surface.

Peptides with desired binding properties can then be isolated from the transformants identified in step (d) by isolating the fusion protein produced by the transformant via immobilization on a solid support through a specific carrier protein/support group interaction; and cleaving said peptide from said fusion protein by treatment with a protease specific for said proteolytic cleavage site in said fusion protein.

In a preferred embodiment of the invention, the random peptides are presented with a free carboxy terminus after immobilization on a solid support and screened with a soluble receptor or other molecular recognition element (MRE). By the methods of the present invention, any tripartite fusion protein identified as possessing a desired property can be readily converted into free soluble peptide, facilitating the detailed pharmacological analysis of peptide leads. Methods for the generation of peptide diversity around a lead are also described that involve the deliberate misincorporation of nucleotides encoding the peptides. Methods for both the large-scale production (10 mg) of peptides or the small scale production (10 µg) of hundreds to thousands of different free soluble peptides are also described.

In addition, the present invention provides a number of specific conformationally constrained molecular scaffolds around which to build peptide diversity. The scaffolding structures are encoded by novel nucleic acid molecules that can be incorporated into not only the present random peptide generation and display system but also the systems known in the prior art. These novel nucleic acids also provide expression vectors, transformed host cells, and peptides of the invention. The C-terminal chimeric fusion peptide approach (utilizing the ability to screen large numbers of peptides and subsequently to produce free soluble versions of the peptides of interest) is the ideal system for building peptide diversity around pharmacologically relevant molecular scaffolds.

The present invention also provides recombinant DNA vectors useful for constructing random peptide libraries, random peptide libraries composed of recombinant DNA expression vectors and host cells transformed with those vectors, and fusion proteins expressed by the host cells of the library.

BRIEF DESCRIPTION OF THE DRAWINGS

FIG. 4, in two parts designated

FIG. 5 shows the nucleotide sequence of the random peptide encoding region of 16 different recombinants from a dynorphin B misincorporation library.

FIG. 6 shows the amino acid sequences encoded by the 16 different recombinants described in FIG. 5.

DESCRIPTION OF THE SPECIFIC EMBODIMENTS

Figure 1:
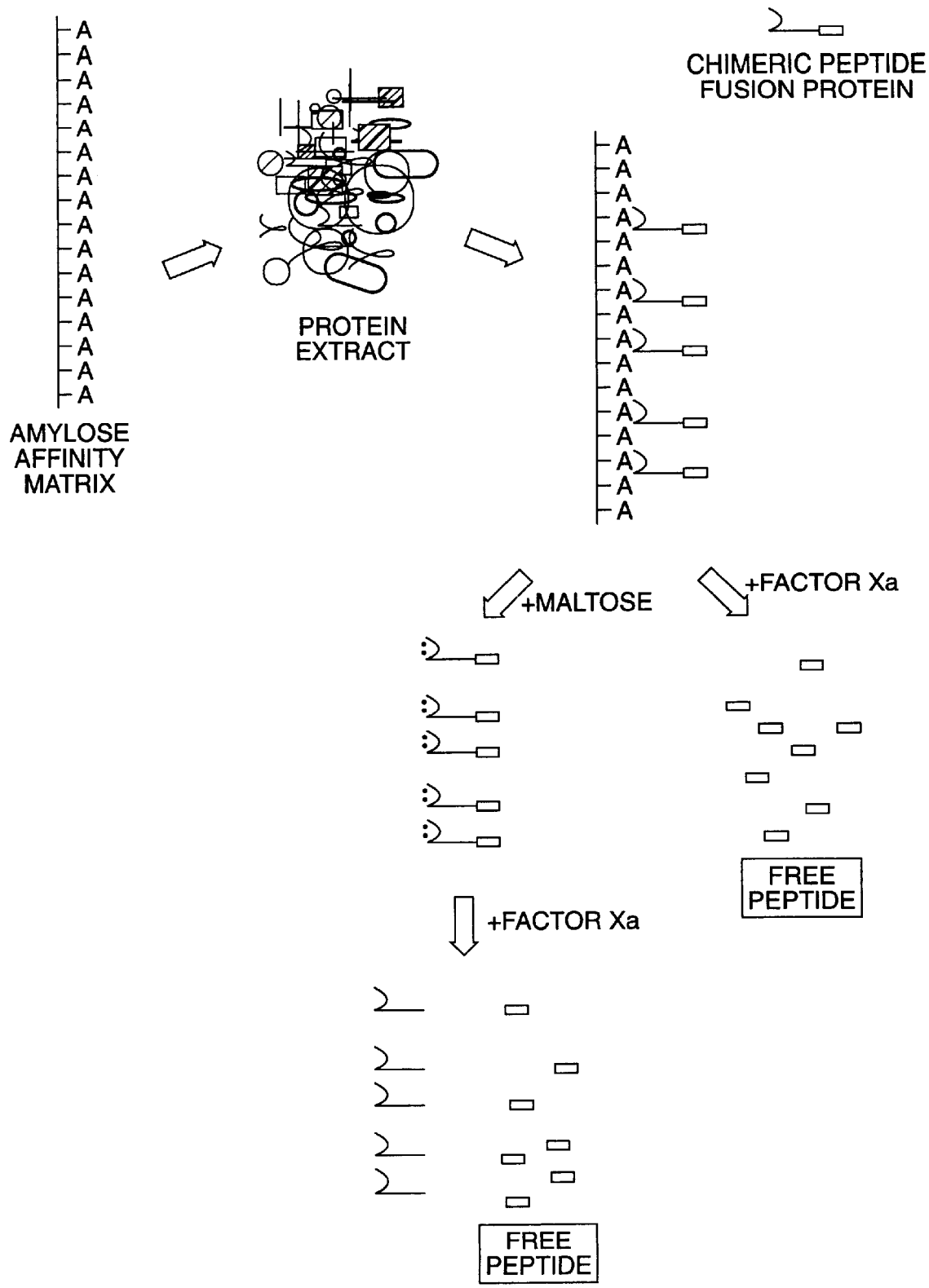
FIG. 1 shows a schematic for the affinity purification of a fusion protein of the invention on a solid support of amylose (starch) resin and the subsequent elution of the purified fusion protein by the addition of maltose.

For purposes of clarity and a complete understanding of the invention, the following terms are defined.

"Carrier Protein" refers to a soluble protein that can be produced at high levels in a host cell; promotes protection from proteases to random peptide fused to the carrier protein; can be immobilized on a solid support derivatized with or composed of an affinity reagent that specifically interacts with and binds to the carrier protein; and can be used for the facile determination of the three dimensional structure of the associated random peptide.

"Epitope" refers to that portion of an antigen that interacts with an antibody.

"Host Cell" refers to a eukaryotic or procaryotic cell or group of cells that can be or has been transformed by a recombinant DNA vector. For purposes of the present invention, a host cell is typically an *E. coli* cell, such as an *E. coli* B cell.

"Ligand" refers to a molecule, such as a random peptide, that is recognized by a particular receptor.

"Linker" or "spacer" refers to a molecule or group of molecules that connects two molecules, such as a carrier protein and a random peptide, and serves to place the two molecules in a preferred configuration, e.g., so that the random peptide can bind to a receptor with minimal steric hindrance from the carrier protein.

"Peptide" or "polypeptide" refers to a polymer in which the monomers are alpha-(L)-amino acids joined together through amide bonds. Peptides are at least two and usually three or more amino acid monomers long. Standard abbreviations for amino acids are used herein (see Stryer, 1988, Biochemistry, Third Ed., incorporated herein by reference.)

"Random Peptide" refers to an oligomer composed of two or more amino acid monomers and constructed by a means with which one does not preselect the complete sequence of a particular oligomer.

"Random Peptide Library" refers not only to a set of recombinant DNA vectors (also called recombinants) that encodes a set of random peptides, but also to the set of random peptides encoded by those vectors, as well as the fusion proteins containing those random peptides.

"Receptor" refers to a molecule that has an affinity for a given ligand. Receptors can be naturally occurring or synthetic molecules. Receptors can be employed in an unaltered state or as aggregates with other species. Receptors can be attached, covalently or noncovalently, to a support, either directly or via a linking substance. Examples of receptors include, but are not limited to, antibodies, including monoclonal antibodies and antisera reactive with specific antigenic determinants (such as the determinants on viruses, cells, or other materials), cell membrane receptors, enzymes, and hormone receptors. In a broader sense, the term "receptors" also refers to molecules such as nucleic acids, carbohydrates, lipids, and dyes that can bind specifically to a ligand.

"Recombinant DNA Vector" refers to a DNA or RNA molecule that encodes a useful function and can be used to transform a host cell. For purposes of the present invention, a recombinant DNA vector typically is a phage or plasmid and can be extrachromosomally maintained in a host cell or integrated into the host cell chromosomal DNA.

The peptide library of the invention is constructed so that the peptide is expressed as a tripartite chimeric fusion product: (1) the random peptide is fused to a (2) carrier protein through a (3) proteolytic cleavage site. The method of generating the peptide library therefore comprises the steps of (a) constructing a set of recombinant DNA vectors that encodes a fusion protein composed of a carrier protein fused to a random peptide through a sequence that encodes a proteolytic cleavage site; (b) transforming host cells with the vectors of step (a); and (c) culturing the host cells transformed in step (b) under conditions suitable for expression and display of the fusion proteins. The set of vectors will typically include at least one thousand different members and often more than one million different members. Each of the three components of the tripartite fusion protein performs an important role in certain aspects of the present invention, yet each component can also be varied to provide a rich diversity of embodiments of the invention.

The carrier protein serves to enhance the production of the associated random peptide and provide for the affinity purification of the random peptide. The carrier protein and the nucleic acid sequences that code for the expression of the carrier protein also act to enhance production by providing effective translation signals and protection from peptidases and maintaining solubility at high expression levels. The carrier protein can also aid in the structural characterization of the associated peptide. For example, if the carrier protein has been characterized by NMR or X-ray crystallography, then the carrier protein can provide a basis for the comparative analysis of the tripartite fusion product.

One very important property of the carrier protein relates to one's ability to immobilize the carrier protein (and so the tripartite fusion product) on a solid support by binding the carrier protein to the solid support through an affinity reagent. The availability of affinity reagents for the carrier protein allows not only the solid support presentation of libraries but also the affinity purification of the peptide fusion proteins. Preferred carrier proteins for purposes of the present invention include the maltose binding protein; streptavidin; $(His)_n$, where n is 3 or more; ubiquitin; the cellulose binding protein; and glutathione-S-transferase.

In a preferred embodiment, the present invention provides a random peptide expression system based on the production of a fusion protein composed of the maltose binding protein (MBP), the Factor Xa cleavage sequence, and a random peptide. MBP is the product of the malE gene of *E. coli* and allows the affinity purification of the fusion protein on a solid support of amylose (starch) resin and the subsequent elution of the purified fusion by the addition of maltose (see FIG. 1). Expression systems based on the MBP gene have been developed (see di Guan et al., 1988, *Gene* 67: 21–30; Maina et al., 1988, *Gene* 74: 365–373; Riggs, 1990, *Curr. Prot. Molec. Biol.* (Ausubel et al., eds.); and Bedouelle and Duplay, 1988, *Eur. J. Biochem.* 171: 541–549, each of which is incorporated herein by reference) and are available commercially (New England Biolabs).

In another preferred embodiment of the invention, streptavidin is the carrier protein, and either the enterokinase or the Factor Xa recognition sequence serves as the carrier protein/random peptide linkage. Biotin or iminobiotin (Pierce Chemical Co.) conjugated solid supports can be used for the affinity matrix purification. Depending on the application, biotin (with a $K_d$ of ~$10^{-15}$ M for streptavidin) or iminobiotin (the guanido analog with a much lower $K_d$) can be used (see Sano and Cantor, 1990, *Proc. Natl. Acad. Sci. USA* 87:142–146, and Sano and Cantor, 1991, *BBRC* 176:571–577, each of which is incorporated herein by reference). In a third preferred embodiment of the invention, the carrier protein is a single triplet of histidine residues. Affinity matrix purification of fusion proteins comprising this carrier protein is via a metal chealate adsorbant ($Ni^{2+}$-NTA or $Ni^{2+}$-IDA); see Hochuli et al., Nov. 1988, *Biotechnology*, pages 1321–1325, and Smith et al., 1988, *J. Biol. Chem.* 263:7211–7215, each of which is incorporated herein by reference). Other carrier proteins of the invention include ubiquitin (see Yoo et al., 1989, *J. Biol. Chem.* 264: 17078–17083, incorporated herein by reference), the cellulose binding protein of *E. coli* (see ong et al., 1989, *Biotechnology* 7: 604–607, incorporated herein by reference), and glutathione-S-transferase (see Smith and Johnson, 1988, *Gene* 67: 31–40, incorporated herein by reference).

The carrier protein is fused to the random peptide through a proteolytic cleavage site. The function of the proteolytic cleavage site is to allow the release of the peptide moiety from the carrier domain after the purification and/or immobilization of the fusion chimera. Some proteolytic cleavage site motifs, such as the enterokinase and the collagenase proteolytic cleavage sites, are cleaved within the motif, which results in extraneous amino acids at the end of the peptide produced by the cleavage. The presence of these extraneous amino acid residues will be unnecessary or undesired in some circumstances. However, other proteases cleave downstream of the motif, yielding a peptide without any extraneous amino acids.

To date, proteases of the second type, those that cleave downstream of the motif, cleave at a site located at the carboxy-terminal side of the motif. With such proteases, one can produce a random peptide without extraneous amino acids by placing the random peptide coding sequences such that the random peptide is located at the carboxy terminus of the protein. With other proteases, using the corresponding proteolytic cleavage site motifs for those proteases, one can produce random peptides at the amino terminal end of the fusion protein and then cleave those random peptides to produce random peptides with a non-random (motif-related) carboxy terminus. Preferred proteolytic cleavage sites of the former type for release of the peptide moiety for purposes of the present invention include the Factor Xa cleavage site.

Factor Xa cleaves after the tetrapeptide Ile-Glu-Gly-Arg (SEQ ID No 1). The advantage of Factor Xa cleavage over that mediated by other proteases is that the cleavage occurs downstream of the recognition site (rather than within the recognition motif as with enterokinase (Asp-Asp-Asp-Lys) (SEQ ID NO 2) or collagenase (Pro-Val-Gly-Pro) (SEQ ID NO 3) and results in a free peptide without any extraneous amino acid residues. Factor Xa protease is commercially available (New England Biolabs, Danex Biotek, Medac, and Pierce) and cleaves at a w/w ratio of 0.1% to 5%, with an average value (for a typical fusion) of 1%. For example, a random peptide the size of dynorphin B will be approximately 3.5% of the fusion protein in one embodiment of the present invention (13 amino acids at 110 daltons per amino acid onto the MBP/Xa domains of 40 kilodaltons). To generate 3 mg of peptide, one needs to digest about 100 mg of fusion protein, which requires about 1 mg of enzyme.

The number of different embodiments of the invention resulting from various combinations of proteolytic cleavage sites and carrier proteins is increased significantly by the different types of "random peptides" that can be constructed by the present methods. The random peptide moiety can be: specified exactly, completely random, composed of the products of building variation around a core or lead sequence, either immobilized or a free peptide, or presented in a molecular scaffolding structure. Typically, the random peptide will be five to fifty amino acids in length, usually eight to twenty amino acids in length, and may also contain framework or scaffolding structures. Those of skill in the art recognize that the term "random", as used in the phrase "random peptide", does not necessarily mean that a completely unspecified nucleotide sequence was used to generate the random peptide.

For instance, one basic random peptide approach involves building variation around a peptide "lead." In this approach, one starts with a particular peptide sequence, the lead, which may have been selected by some other random peptide approach, such as the peptides on phage approach, discussed above. One then synthesizes in vitro (e.g., with an automated DNA synthesizer) a family of oligonucleotides that is based on the coding sequence of the lead peptide. Each member of the family varies to a particular degree from the original sequence. Sources of leads include (1) quasi-random peptides encoded by $(NNK)_x$, as discussed further below; (2) small peptide encoding DNAs derived from the genes for the natural ligands; (3) the related approach of rearranging small peptide-encoding fragments to produce novel combinations of oligopeptides; (4) the peptide-encoding oligonucleotides from the genomes of fd phage expressing pIII variants; (5) peptide leads from other sources of peptide diversity and characterization that involve the intracellular generation of peptide diversity and detection of peptide-protein interactions via the reconstitution of a viable transcriptional transactivator (see, Field and Song, Jul. 20, 1989, *Nature* 340 (6230):245–246, incorporated herein by reference); and (6) diverse peptides built around a specific conformationally constrained molecular scaffold.

Yet another approach for diversifying a selected random peptide vector involves the mutagenesis of a pool, or subset, of recovered vectors. Recombinant host cells transformed with vectors identified by screening are pooled and isolated. The vector DNA, or a portion of the vector DNA, is mutagenized by treating the cells with, e.g., nitrous acid, formic acid, hydrazine, or by use of a mutator strain such as mutD5 (see Schaaper, 1988, *Proc. Natl. Acad. Sci. USA* 85:8126–8130, incorporated herein by reference). These treatments produce a variety of mutations in the vector DNA. The segment containing the sequence encoding the variable peptide can optionally be isolated by cutting with restriction nuclease(s) specific for sites flanking the variable region and then recloned into undamaged vector DNA. Alternatively, the mutagenized vectors can be used without recloning of the mutagenized random peptide coding sequence.

One can also diversify a selected peptide by misincorporation of nucleotide changes in the coding sequence for the peptide with the polymerase chain reaction (PCR; see U.S. Pat. Nos. 4,683,202; 4,683,195; and 4,965,188, each of which is incorporated herein by reference) under low fidelity conditions. A protocol described in Leung et al., 1989, *Technique* 1:11–15, incorporated herein by reference, utilizes altered ratios of nucleotides and the addition of manganese ions to produce a 2% mutation frequency.

As the PCR misincorporation method shows, various approaches for building variation around a lead peptide involve a nucleotide misincorporation strategy. In one approach, the positive vectors (those identified in a screening method) are sequenced to determine the identity of the active peptides. Oligonucleotides are then synthesized based on these peptide sequences, employing a low level of all bases incorporated at each step to produce slight variations of the primary oligonucleotide sequences. This mixture of (slightly) degenerate oligonucleotides is then cloned into the random peptide library expression vector as described herein. This method produces systematic, controlled variations of the starting peptide sequences but requires, however, that individual positive vectors be sequenced before mutagenesis. This method is useful for expanding the diversity of small numbers of recovered vectors.

One can also use extensive mutagenesis to generate a large number of peptides with a significant number of differences from the lead (as well as generating peptides with few or no differences from the lead). In another approach, single amino acid substitutions in the peptide are favored, and the goal is to find a number of single amino acid differences that either abolish or significantly improve binding. For example, one approach involves the synthesis of four mixtures of nucleotides—each containing one of the four nucleotides at 85%, and each of the other three nucleotides at 5% each. Thus, at each position during solid phase chemical synthesis there is an 85% chance that the "correct" nucleotide will be incorporated and a 15% chance that one of the other three nucleotides will be incorporated (a 5% chance for each). Thus, on average, if one synthesizes an oligonucleotide 100 bases long, then in an average molecule 85% of the nucleotide positions will be correct (that is, will match the lead sequence), and 15% of the positions will have incorporated an incorrect nucleotide compared to the original sequence. Depending on the misincorporation criteria that are selected, the resulting mixture of different oligonucleotides can be quite similar to the core starting sequence, for example by following a 97%1%/1%/1% misincorporation strategy, or quite diverged, on average, from the lead sequence, for example by following a 55%/15%/15%/15% strategy. In any of these approaches, misincorporation statistics can be helpful in determining the number of different variations a particular approach will generate.

With a misincorporation strategy in which there is a 70% chance of the correct nucleotide being incorporated and a 30% chance of one of the other three nucleotides being incorporated (a 10% chance for each), the following table of relative probabilities can be derived. In the table, R refers to the correct nucleotide being incorporated (Right), and W refers to one of the other three nucleotides being incorporated (Wrong).

TABLE 1

Relative Probabilities For a 70/30 Misincorporation Strategy

| Codon status | Individual probabilities | Product of Individual probabilities | Sum of probabilities for group |
|---|---|---|---|
| R R R | (0.7) (0.7) (0.7) | 0.343 | 0.343 |
| R R W | (0.7) (0.7) (0.3) | 0.147 | 0.441 |
| R W R | | | |
| W R R | | | |
| R W W | (0.7) (0.3) (0.3) | 0.063 | 0.189 |
| W R W | | | |
| W W R | | | |
| W W W | (0.3) (0.3) (0.3) | 0.027 | 0.027 |

In summary, for each codon, there is a 34% chance that the codon will be of the wild-type form, a 44% chance the codon will have a single nucleotide change from wild-type, a 19% chance that the will have two changes from wild-type, and a 3% chance that all three nucleotide positions in the codon are different from wild-type.

To illustrate this aspect of the invention, variant random peptides can be built around the peptide dynorphin B. Dynorphin B is a peptide composed of 13 amino acids from the carboxy terminus of the β-neoendorphin/dynorphin precursor. Dynorphin B begins with YGGFL (SEQ ID NO 4) (using the standard one letter abbreviation for amino acid residues), as does Leuenkephalin, and was first described by Fischli et al. in 1982. A highly specific monoclonal antibody to dynorphin B has been isolated and characterized (see Barret and Goldstein, 1985, *Neuropeptides* 6: 113–120, incorporated herein by reference).

The basic approach involves the synthesis of a pool of oligonucleotides that are based on a nucleotide sequence encoding dynorphin B but in which individual oligonucleotides differ at one or more positions from the lead sequence. The following tables demonstrate some statistical and distributional features of the oligonucleotide pool using a misincorporation strategy of 70%/10%/10%/10%. The first of these tables, Table 2, shows the dynorphin B peptide sequence in one-letter and three-letter code on the first and second lines. The third through the fifth lines show for each nucleotide position the probability for the incorporation of a nucleotide that results in the correct amino acid being selected (using the misincorporation stategy of 70% of the correct nucleotide and 30% of an equimolar mixture of the three others). For example, the third position wobble in the case of Gly (amino acids 2 and 3 below) results in any substitution at the third position of the codon retaining Gly specificity, thus a probability of 1. However any change at either of the first two positions of the codon changes the specified amino acid. Similarly, in the case of the third position of the Tyr amino acid codon, a change from the C to a T still specifies Tyr, but a change to G or A changes the amino acid specified, thus a probability of 0.8 (0.7+0.1).

The sixth line shows a nucleotide sequence that encodes the dynorphin B peptide with codons that have been chosen for high expression in *E. coli*. The seventh through eleventh lines show the alternate codons that encode the same amino acids as above. The twelfth line shows for each amino acid position the probability for the incorporation of the same amino acid as in the wild-type sequence. This statistic is derived from the product of the individual nucleotide probabilities shown in third through the fifth lines.

TABLE 2

Statistical/Distributional Analysis—Dynorphin B

| Y | G | G | F | L | R | R | Q | F | K | V | V | T | (SEQ ID NO 5) |
|---|---|---|---|---|---|---|---|---|---|---|---|---|---|
| Tyr | Gly | Gly | Phe | Leu | Arg | Arg | Gln | Phe | Lys | Val | Val | Thr | |
| .7 | .7 | .7 | .7 | ~.8 | ~.75 | ~.75 | .7 | .7 | .7 | .7 | .7 | .7 | |
| .7 | .7 | .7 | .7 | .7 | .7 | .7 | .7 | .7 | .7 | .7 | .7 | .7 | |
| .8 | 1 | 1 | .8 | 1 | 1 | 1 | .8 | .8 | .8 | .1 | .1 | .1 | |
| TAC | GGT | GGT | TTC | CTG | CGT | CGT | CAG | TTC | AAA | GTT | GTT | ACC | |
| TAT | GGA | GGA | TTT | CTT | CGC | CGC | CAA | TTT | AAG | GTC | GTC | ACT | |
| | GGC | GGC | | CTC | CGA | CGA | | | | GTA | GTA | ACA | |
| | GGG | GGG | | CTA | CGG | CGG | | | | GTG | GTG | ACG | |
| | | | | TTA | AGA | AGA | | | | | | | |
| | | | | TTG | AGG | AGG | | | | | | | |
| .39 | .49 | .49 | .39 | .56 | .53 | .53 | .39 | .39 | .39 | .49 | .49 | .49 | |

Given a misincorporation strategy in which there is a 70% chance that the correct nucleotide will be incorporated and a 30% chance that one of the other three nucleotides will be incorporated, the probability that a perfectly correct nucleotide sequence for dynorphin B will be generated is $(0.7)^{39}$ or $9 \times 10^{-7}$, approximately one in a million. Given the redundancy of the genetic code, the chance that a perfectly correct amino acid sequence for dynorphin B is generated, using the same nucleotide misincorporation stategy, is the product of the probabilities shown in the Table (lines three to five and 12), or $4 \times 10^{-5}$, approximately one in 25,000.

The average percent nucleotide misincorporation for an encoded peptide in the illustrative library described above is 0.3. At the amino acid level, the approximate average number of amino acid changes per peptide is 0.46 (the mean of the individual probabilities at each position). On average then, half of the amino acids will be unchanged and half will have changed. Because of differential redundancy among amino acids, some positions are more likely to undergo a change than others.

Because the 46% average misincorporation is so close to 50%, one can assume a binomial distribution and apply Bernoulli trials to approach an approximation of the distribution of misincorporation types (i.e., how many peptides will have one change, how many will have two, etc.) The base of Pascal's triangle for n=13 yields the information presented in tabular form below.

TABLE 3

Distribution of Misincorporation Types

| 0 | 1 | 2 | 3 | 4 | 5 | 6 | 7 | 8 | 9 | 10 | 11 | 12 | 13 |
|---|---|---|---|---|---|---|---|---|---|---|---|---|---|
| $10^{-4}$ | .002 | .01 | .04 | .09 | .16 | .21 | .21 | .16 | .09 | .04 | .01 | .002 | $10^{-4}$ |
| 12 | 200 | $10^3$ | $4 \times 10^3$ | $9 \times 10^3$ | $16 \times 10^3$ | $21 \times 10^3$ | $21 \times 10^3$ | $16 \times 10^3$ | $9 \times 10^3$ | $4 \times 10^3$ | $10^3$ | 200 | 12 |

In the table, the top row lists the number of amino acid changes from wild-type (i.e., no changes, one change, etc.), and the second row lists the probability for each of the change types. The third row lists the number of each type expected in a library of 100,000 recombinants. Thus, over 90% of the peptides will contain between 4 and 9 changes from wild-type, but there will be some (1 in 10,000) that have no changes.

Examples of the amino acid diversity that results from all possible single nucleotide changes is shown with glutamine (found at position 8 in dynorphin B, an amino acid with only two codons) and arginine (found at positions 6 and 7 in dynorphin B, an amino acid with six codons), in Table 4 below.

TABLE 4

Single Nucleotide Changes—Effect on Diversity

| G/n | Arg |
|---|---|
| CAG Gln | CGT Arg |
| AAG Lys | AGT Ser |
| GAG Glu | GGT Gly |
| TAG Stop | TGT Cys |
| CCG Pro | CAT His |

TABLE 4-continued

Single Nucleotide Changes—Effect on Diversity

| G/n | Arg |
|---|---|
| CGG Arg | CCT Pro |
| CTG Leu | CTT Leu |
| CAA Gln | CGA Arg |
| CAC His | CGC Arg |
| CAT His | CGG Arg |

Two nucleotide changes per codon result in much greater diversity of the resulting codons. Thus, in the case of Gln (CAG) two nucleotide changes can specify all other amino acids except for Cys and Ile, and in the case of Arg (CGT), two nucleotide changes can specify all other amino acids except for Glu, Lys, and Met.

As shown above, stop codons can arise from single nucleotide changes of the Tyr codon TAC (amino acid #1), and the Gln codon CAG (amino acid #8). Stop codons from two-nucleotide changes can arise from: Phe, TTC; Gly, GGT; Arg, CGT; Leu, CTG; and Lys, AAA. Thus single nucleotide changes can convert 2 of the 13 codons to terminators and two nucleotide changes can convert an additional 5 amino acids accounting for 8 residues of dynorphin B to terminators. Thus, 10 of the 13 positions can be converted to stop codons via either a one or two nucleotide change, a situation occuring in approximately 63% of the codons when utilizing a 70%/30% nucleotide misincorporation strategy. All possible truncation molecules will occur at some frequency, and certain stop codons should be prevalent in the total sample. When the vectors of the invention that allow for C-terminal presentation of random peptides are used, the presence of stop codons does not affect the expression of the carrier portion of the tripartite fusion protein of the present invention. Thus, the present method can be used to generate structure activity relationship (SAR) information for deletions as well as substitutions in a lead peptide.

Like stop codons, the presence of "rare" codons can have a major effect on the expression of a particular fusion protein. Alternative synonomous codons are not used with equal frequency in genes (reviewed in Sharp et al., 1987, *Nuc. Acids Res.* 16: 8207–8211, incorporated herein by reference). Codon usage patterns are quite species specific and so are used for comparative analyses in molecular evolution studies. For example, of the four synonomous codons of proline (CCN) in the *E. coli* genome, CCG is found 170 times more frequently than CCC. The RSCU values for proline (observed number of codons divided by the number expected if all codons for that amino acid were used equally) are: CCG, 3.41; CCA, 0.42; CCU, 0.15; and CCC, 0.02. For another example, ACU and ACC are used for threonine 20 times more frequently than ACA and ACG (RSCU values of 1.87 and 1.91 and 0.10 and 0.12, respectively). Differential utilization of codons is much more dramatic in genes that are expressed at a high level as opposed to genes expressed at low levels. There is a correlation between the codons used frequently in highly expressed genes and the relative amounts of the corresponding charged tRNAs.

Codon usage may also affect expression levels by the effect certain codons may have on the formation, activity, and half-life of the RNA transcripts containing the codon. Thus, there will be some differences in expression levels for a given peptide depending upon the codons that encode the peptide. Differential expression should not be a problem in solid support screening. However, when numbers of soluble peptides are being produced en masse for subsequent pharmocologic and cell biological studies, one may desire to avoid the use of rare codons.

For implementation of a misincorporation approach, the limitations of the DNA synthesizer need to be taken into consideration. To illustrate, the ABI model 491 has only 5 ports for reagent entry, and any machine driven mixing of reagents must be done on an equal volume basis (i.e. 50/50 from two of the reagent bottles; 25/25/25/25 from four of the reagent bottles, etc.) Thus, one approach uses the first four reagent bottles for each of the individual bases (A, C, G, and T) and the fifth for an equimolar mixture of all four bases. However a 50/50 mixture of any of the first four bottles with the mixture in reagent bottle port 5 will yield 62.5%/12.5%/12.5%/12.5%. One could also lower the concentration of the four nucleotide mixture in reagent bottle 5. For example, if one lowers the total nucleotide concentration in reagent bottle 5 to $\frac{2}{3}$ of that in the single nucleotide bottles, a 50/50 mixture of port 5 with each of the other ports yields the desired 70/10/10/10.

The general formula for a given misincorporation strategy is $(1+0.25x)$ divided by $(1+x)=y$, where x is the fractional concentration of reagent bottle 5 relative to the standard concentration in each of the first four bottles, and y is the desired relative concentration value for the majority member of the misincorporation strategy (e.g. 0.7 in 70/10/10/10). Rearranging the formula for ease of use yields: $(y-1)$ divided by $(0.25-y)=x$.

Of course, the benefits provided by the present invention are useful not only for building variation around a lead peptide using a misincorporation strategy but also for using information from the structure of known ligands to find new peptide ligands having features modified from those of the known ligand. In this embodiment of the invention, fragments of a gene encoding a known ligand, prepared by, e.g., limited DNAse digestion into pieces of 20 to 100 base pairs, are subcloned into a variable nucleotide region system as described herein either singly or in random combinations of several fragments. The fragment library is then screened in accordance with the procedures herein to identify small peptides capable of binding to a receptor and having characteristics which differ as desired from the parental peptide ligand. This method is useful for screening for any receptor-ligand interaction where one or both members are encoded by a gene, e.g., growth factors, hormones, cytokines, and the like, such as insulin, interleukins, insulin-like growth factor, etc. In this embodiment of the invention, the peptide library can contain as few as 10 to 100 different members, although libraries of 1000 or more members can also be used.

In another useful embodiment of the invention, one can use the present method to build completely random peptides and quasi-random peptides. The size of such libraries will vary according to the number of variable codons, and hence the size of the peptides, that are desired. Generally, the library will be at least $10^6$ to $10^8$ or more members, although smaller libraries may be quite useful in some circumstances. To generate a collection of oligonucleotides that forms a series of codons encoding a random collection of amino acids, a codon motif is used, such as $(NNK)_x$, where N may be A, C, G, or T (nominally equimolar), K is G or T (nominally equimolar), and x is typically up to about 5, 6, 7, or 8 or more, thereby producing libraries of penta-, hexa-, hepta-, and octa-peptides or more. The third position can alternatively be G or C, designated "S".

There are 32 possible codons resulting from the NNK motif: 1 for each of 12 amino acids, 2 for each of 5 amino acids, 3 for each of 3 amino acids, and only one of the three stop codons. Thus, NNK or NNS (i) code for all the amino acids, (ii) code for only one stop codon, and (iii) reduce the range of codon bias from 6:1 to 3:1. Although this motif produces a codon distribution as equitable as available with standard methods of oligonucleotide synthesis, it results in a bias against peptides containing one-codon residues. For example, a complete collection of hexacodons contains one sequence encoding each peptide made up of only one-codon amino acids, but contains 729 ($3^6$) sequences encoding each peptide with three-codon amino acids. With longer peptides, the size of the library that is generated can become a constraint in the cloning process, but the larger libraries can be sampled, as described below. The expression of peptides from randomly generated mixtures of oligonucleotides in recombinant vectors is discussed in Oliphant et al., 1986, *Gene* 44:177–183, incorporated herein by reference. See also, Arkin and Youvan, 1992, *Biotechnology* 10:297–300, incorporated herein by reference.

An alternate approach that minimizes the bias against one-codon residues involves the synthesis of 20 activated trinucleotides, each representing the codon for one of the 20 genetically encoded amino acids. These trinucleotides are synthesized by conventional means, removed from the support with the base and 5-OH-protecting groups intact, and activated by the addition of 3'-O-phosphoramidite (and phosphate protection with beta-cyanoethyl groups) by the method used for the activation of mononucleosides, as generally described in McBride and Caruthers, 1983, *Tetr. Letters* 22:245, which is incorporated herein by reference.

Degenerate "oligocodons" are prepared using these trimers as building blocks. The trimers are mixed at the desired molar ratios and installed in the synthesizer. The ratios will usually be approximately equimolar, but may be a controlled unequal ratio to obtain the desired over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, 1984, *OliQonucleotide Synthesis* (M. J. Gait, ed.) pp. 35–82, incorporated herein by reference. This procedure generates a population of oligonucleotides for cloning that is capable of encoding an equal distribution (or a controlled unequal distribution) of the possible peptide sequences. This approach may be especially useful in generating longer peptide sequences, because the range of bias produced by the $(NNK)_x$ motif increases by three-fold with each additional amino acid residue.

In a related method, a completely random, unbiased DNA library can be prepared by the following method: (a) one codon sequence is chosen for each of the twenty naturally occurring, genetically encoded amino acids; (b) twenty, one for each codon, DNA synthesis columns are respectively marked to indicate the codon to be synthesized therein; (c) the DNA synthesizer is programmed so that each different codon is synthesized in a different column (i.e., column 1 is programmed to synthesize 5'-AGC-3', a serine codon; column 2 is programmed to synthesize 5'-CGT-3', an alanine codon; and so on); (d) each codon is then synthesized in its respective column; (e) after synthesis, all 20 columns are opened, and the resins combined and then redistributed equally to the 20 columns; and (f) steps (d) and (e) are repeated the number of times required to obtain an oligonucleotide that encodes a random peptide of the length desired. With this technique, one can also prepare libraries biased to contain only certain amino acids. For example, one can eliminate tryptophan or cysteine from the random peptides in the library or prepare a library that only encodes hydrophobic amino acids. Mutagenesis strategies might entail preparing libraries in which all 20 amino acids are present in some positions, but only two or three critical residues are present at other positions. Furthermore, by restricting the number of oligonucleotides synthesized, one can actually prepare more complete libraries. One can ensure that all possible combinations are represented by preparing several different libraries with restricted codon diversity.

Another related method uses fewer than 20 columns to generate the oligonucleotides and is based on the employment of controlled degeneracy, so that each column produces specific codons for several amino acids. The simplest example is the production of equal amounts of the codons for four different amino acids (and no stop codons) on each of five columns. In this example, the first column is programmed to synthesize "TKK", yielding codons for F, L, C, and W amino acids; the second column is programmed to synthesize "MMG" (where M is C or A), yielding codons for P, Q, T, and K amino acids; the third column is programmed to synthesize "NAT", yielding codons for Y, H, N, and D amino acids; the fourth column is programmed to synthesize "GNG", yielding codons for V, A, E, and G amino acids; and the fifth column is programmed to synthesize "AKK", yielding codons for I, M, S, and R amino acids. After each round of synthesis, the resins from the five columns are mixed and redistributed to five columns and the process repeated until an oligo-codon of the desired length is prepared. Each column should produce the same number of codons as the other columns to avoid biasing the representation of the amino acids.

In another embodiment, only four columns are used: (1) "DKG", where D is T, A, or G; (2) "VMG", where V is C, A, or G; (3) "NAT"; and (4) "WKT", where W is T or A. In this embodiment, columns one and two each produce codons for six amino acids, and columns three and four each produce codons for four amino acids. The omission of amino acid residues requires a case-by-case analysis and may require the omission of an accompanying amino acid. For an example based on the five column method, any of the residues synthesized on column three (Y, H, N, or D) can be deleted individually. To remove Y, for example, the codon synthesis is "VAT". Any of the residues on column four can be deleted in similar fashion.

Cases where deletion is more difficult are residues made on columns one, two, and five. For example, if one desires to remove W from any (or all) positions, then one would use the codon scheme "TTK", giving amino acids F and L, or "TKT", giving amino acids F and C, thus losing either C or L along with the desired loss of W. There are means to obtain only the desired deletion. In the previous example, the W can be replaced by a stop codon using the motif "TKW".

To facilitate the construction of libraries designed to lack one or more specific amino acids at one or more positions, the following seven column scheme may be employed. The theme for this approach is the varying of only one base in each triplet. The seven columns are respectively programmed to synthesize the codons defined by: (1) "TDT"; (2) "TBT", where B is T, G, or C; (3) "GVT"; (4) "VAG"; (5) "AHT", where H is A, C, or T; (6) "GVT"; and (7) "RTG", where R is A or G. The codons made in column seven will be slightly over-represented, with codons for M and V present 1.5 times more than the other codons. With this method, any amino acid can be excluded at any position by excluding the appropriate base from the codon. This results in over-representation of the remaining two codons produced by that column (1.5×). In the occasional case where two amino acids are excluded from a single column, a more significant bias in favor of the remaining amino acid codon results (3×). In some cases, this remaining amino acid can be synthesized as part of another codon set, eliminating the bias and reducing to six the number of columns required.

With the basic random peptide oligocodon, in which the codon motif is $(NNK)_x$, as defined above, and when x equals 8, there are $2.6 \times 10^{10}$ possible octapeptides. A library containing most of the octapeptides may be difficult to produce. Thus, a sampling of the octapeptides may be accomplished by constructing a subset library using about 0.1%, and up to as much as 1%, 5%, or 10%, of the possible sequences, which subset of recombinant vectors is then screened. As the library size increases, smaller percentages are acceptable. If desired to extend the diversity of a subset library, the recovered vector subset may be subjected to mutagenesis and then subjected to subsequent rounds of screening. This mutagenesis step may be accomplished in two general ways: the variable region may be mutagenized or additional variable amino acids may be added to the regions adjoining the initial variable sequences.

The latter approach for diversifying a set of peptide ligands involves the addition of amino acids to a peptide or peptides found to be active. For instance, one can synthesize oligonucleotides that incorporate the lead sequence and an adjoining degenerate sequence. These oligonucleotides are then cloned to produce a secondary library. In another approach that adds a second variable region to a pool of random peptide expression vectors, a restriction site is installed next to the primary variable region. Preferably, the enzyme should cut outside of the recognition sequence, i.e., an enzyme such as BspMI, which cuts leaving a four base 5' overhang, four bases to the 3' side of the recognition site. Thus, the recognition site may be placed four bases from the primary degenerate region. To insert a second variable region, a degenerately synthesized oligonucleotide is then ligated into this site to produce a second variable region juxtaposed to the primary variable region. This secondary library is then amplified and screened.

Using known recombinant DNA techniques (see generally, Sambrook et al., 1989, *Molecular Cloning, A Laboratory Manual*, 2d ed., Cold Spring Harbor Laboratory Press, Cold Spring Harbor, N.Y., 1989, incorporated herein by reference), one can synthesize an oligonucleotide that, inter alia, removes unwanted restriction sites and adds desired ones, reconstructs the correct portions of any sequences that have been removed, inserts the spacer, conserved, or framework residues, if any, and corrects the translation frame (if necessary) to produce an active fusion protein comprised of a carrier protein fused to a random peptide through a proteolytic cleavage site. The oligonucleotide will contain one or more random peptide coding sequences (variable region domain) and may also contain spacer or framework residues. The sequences are ultimately expressed as peptides (with or without spacer or framework residues) fused to or in the carrier protein.

While in some instances one may desire to synthesize peptides having contiguous variable regions to bind certain receptors, in other cases, one may desire to provide peptides having two or more regions of diversity separated by spacer residues. For example, the variable regions may be separated by spacers that allow the diversity domains of the peptides to be presented to the receptor in different ways. The distance between variable regions may be as little as one residue or as many as five to ten to up to about 100 residues. For probing a large binding site, one may construct variable regions separated by a spacer of residues of 20 to 30 amino acids. The number of spacer residues, when present, will preferably be at least two to three or more but usually will be less than eight to ten. An oligonucleotide library having variable domains separated by spacers can be represented by the formula: $(NNK)y-(abc)n-(NNK)z$, where N and K are as defined previously (note that S as defined previously may be substituted for K); y+z is equal to about 5, 6, 7, 8, or more; a, b and c represent the same or different nucleotides comprising a codon encoding spacer amino acids; and n is up to about 20 to 30 or more.

The spacer residues may be somewhat flexible, comprising oligoglycine, for example, to provide the diversity domains of the library with the ability to interact with sites in a large binding site relatively unconstrained by one another or by attachment to the carrier protein. Rigid spacers, such as, e.g., oligoproline, may also be inserted separately or in combination with other spacers, including glycine residues. The variable domains can be close to one another with a spacer serving to orient the one variable domain with respect to the other, such as by employing a turn between the two sequences, as might be provided by a spacer of the sequence Gly-Pro-Gly, for example. To add stability to such a turn, one can add Cys residues at either or both ends of each variable region. The Cys residues would then form disulfide bridges to hold the variable regions together in a loop, and in this fashion may also serve to cause the random peptide to mimic a cyclic peptide, as discussed further below. of course, those skilled in the art will appreciate that various other types of covalent linkages for cyclization may also be accomplished.

The spacer residues described above can also be encoded on either or both ends of the variable nucleotide region. For instance, a cyclic peptide coding sequence can be made without an intervening spacer by having a Cys codon on both ends of the random peptide coding sequence. As above, flexible spacers, e.g., oligoglycine, may facilitate interaction of the random peptide with the selected receptors. Alternatively, rigid spacers may allow the peptide to be presented as if on the end of a rigid arm, where the number of residues, e.g., Pro, determines not only the length of the arm but also the direction for the arm in which the peptide is oriented. Hydrophilic spacers, made up of charged and/or uncharged hydrophilic amino acids, (e.g., Thr, His, Asn, Gln, Arg, Glu, Asp, Met, Lys, etc.), or hydrophobic spacers made up of hydrophobic amino acids (e.g., Phe, Leu, Ile, Gly, Val, Ala, etc.) may be used to present the peptides to binding sites with a variety of local environments.

The present invention can be used to construct improved spacer molecules. For example, one can construct a random peptide library that encodes a carrier protein, a random peptide of formula $(NNK)_5$ (sequences up to and including $(NNK)_{10}$ or $(NNK)_{15}$ could also be used) through a proteolytic cleavage site which random peptide is in turn fused to a peptide ligand of known specificity. One would then screen the library for improved binding of the peptide ligand to the receptor specific for the ligand using the method of the present invention. Fusion proteins that exhibit improved specificity would be isolated as well as the vector that encodes them, and the vector or the spacer encoding portion thereof would be sequenced to determine the structure of the spacer responsible for the improved binding.

Just as spacer molecules can be incorporated into the random peptide fusion proteins of the invention, so too can one incorporate conformational constraints, or scaffolding, into the structure of the peptide library. A number of motifs from known protein and peptide structures can be adapted for this purpose. The method involves introducing nucleotide sequences that code for conserved structural residues into or adjacent to the variable nucleotide region so as to contribute to the desired peptide structure. Positions nonessential to the structure are allowed to vary.

A degenerate peptide library as described herein can incorporate the conserved frameworks to produce and/or identify members of families of bioactive peptides or their binding receptor elements. Several families of bioactive peptides are related by a secondary structure that results in a conserved "framework," which in some cases, as noted above, is a pair of cysteines that flanks a string of variable residues. This results in the display of the variable residues in a loop closed by a disulfide bond. Thus, one type of scaffolding structure provided by the present invention allows one to express cyclic random peptides. By placing cysteines at the ends of the variable region, one can produce pseudo-cyclic peptides upon the formation of disulphide linkages between the cysteines. The production of C-terminal peptide fusions combined with protein export to the periplasm of *E. coli* will allow the Cys residues to undergo disulphide bridge formation, resulting in the cyclization of the random peptide.

A specific application of cyclic peptide scaffolds involves building diversity around endothelin leads. Endothelins are cyclic peptides, but rather than being anchored by a single disulfide bridge, endothelins are anchored by two disulphide bridges and so are actually bicyclic. Endothelins are potent vasoconstrictors produced by mammalian vascular endothelial cells (see Yanagisawa et al., 1988, *Nature* 332: 411–415, incorporated herein by reference). In fact, the endothelins are the most potent mammalian vasoconstrictors known to date (with an EC50 concentration an order of magnitude less than angiotensin II, vasopressin, and neuropeptide Y). Endothelin structure is similar to but distinct from that of the neurotoxins of bee, scorpion, and snake venoms (see Billingham et al., 1973, *Nature* 245: 163–164, incorporated herein by reference). The endothelins play an important role in mammalian vascular homeostasis and are attractive targets for therapeutic intervention.

Another important scaffolding structure of the invention relates to a region characteristic of DNA binding peptides called a "leucine zipper". Peptides corresponding to a region of the leucine zipper class of DNA binding transcriptional transactivators can function as specific DNA binding peptides (see O'Neil et al., 1990, *Science* 249: 774–778, and Talanian et al., 1990, *Science* 249: 769–771, each of which is incorporated herein by reference). This class of proteins is characterized by a motif featuring leucine residues repeated every 7 amino acids. Adjacent to the leucine zipper is the basic region, an alpha helical region rich in lysines and arginines characterized by a conserved helical face and a variable helical face. The leucine zipper sub-domain mediates dimerization, and the basic sub-domain specifically interacts with the DNA double helix.

One can use cysteine residues to substitute for the leucine zipper. The substitution mimics the dimerization mediated by parallel alpha helical coiled coil interactions with a single disulphide bridge. Specific DNA binding will be dependent on the formation of the disulphide. One can therefore use the present invention to construct similar peptides with the conserved framework residues specified and the intervening residues allowed to vary via the misincorporation approach. Use of periplasm directed cloning vectors rather than cytoplasm targeted vectors will promote formation of the requisite disulphide bond. One can then screen for a novel DNA binding specificity in a manner analagous to the screening of lambda gt11 libraries for specific DNA binding proteins (see Singh et al., 1988, Cell 52: 415–423, incorporated herein by reference).

Another DNA binding peptide scaffold structure of the invention is related to zinc fingers. Zinc finger motifs were first identified in the transcription factor TFIIIa by showing that this protein requires zinc for specific DNA binding. Sequence analysis showed the protein contains tandem arrays of linked cysteine and histidine pairs. A model was described in which each of the repeated motifs bound a zinc ion through the invariant pairs (see Miller et al., 1985, EMBO J. 4: 1609–1614, and Brown and Argos, 1986, Nature 324: 215, each of which is incorporated herein by reference). Subsequent spectroscopic, X-ray crystallographic, and NMR analyses confirmed the basic features of the zinc finger model, in which the zinc ligand is tetrahedrally coordinated by the four residues and stabilizes a helical structure that can interact with the major groove of DNA. Although usually present in tandem, repeated copies in proteins, individual finger motifs have been reported to be sufficient for specific DNA binding (see Parraga et al., 1990, Proc. Natl. Acad. Sci. USA 87: 137–141, incorporated herein by reference).

Random peptide libraries built around zinc finger scaffolding motifs may provide a rich source of lead compounds for drug discovery. A number of biologically important proteins contain the zinc finger motif. Although some of skill in the art reserve the use of the term "zinc finger" to only those motifs of the TFIIIa class, as used herein, the term encompasses any zinc coordianted motif. Zinc fingers have been implicated in protein-protein interactions, single stranded DNA binding, and RNA binding (reviewed in Berg et al., 1990, J. Biol. Chem. 265: 6513–6516, incorporated herein by reference). Members of the zinc finger protein gene family play a role in RNA processing (splicing) and DNA replication; for instance, the retroviruses, including HIV, have a variant of the zinc finger motif involved with genome packaging and virus replication. The steroid/thyroid family of nuclear receptors recognize and bind their DNA targets using a variation of the zinc finger motif (see Berg, 1989, Cell 57: 1065–1068, incorporated herein by reference). Target genes turned on by the action of the lymphokines, TNF, IL-1, and gamma-interferon, include zinc finger transcription factors believed to be responsible for mediating the next step of the inflammatory cascade (e.g. the induction of expression of cell adhesion molecules; see Opipari et al., 1990, J. Biol. Chem. 265: 14705–14708, incorporated herein by reference). Zinc finger proteins have also been shown to be associated with the neoplastic phenotype (see Tagawa et al., 1990, J. Biol. Chem. 265: 20021–20026, incorporated herein by reference).

Another molecular scaffold for the presentation of peptide diversity is similar to a motif found in the conotoxin neuropeptides. These are peptide venoms that have been shown to act on calcium channels, sodium channels, acetylcholine receptors and vasopressin receptors. Conotoxins are characterized by their small size (10 to 50 amino acids) and their rigid specific conformation (mediated by the presence of 6 cysteines and 3 disulphide bridges). A key biological result of the rigidity of the peptide structure is that these ligands show great specificity and can discriminate between closely related receptor subtypes.

The predatory snails of the Conus genus have evolved a family of related peptides that are potent venoms targetted to the neuromuscular systems of their prey. In a recent published review of the conotoxins (see Olivera et al., 1990, Science 249: 257–263, incorporated herein by reference), the authors argued that the pharmacological diversity of these venoms could be equivalent to that of the alkaloids of plants and the secondary metabolites of microorganisms. Conotoxin peptides are the smallest nucleic acid encoded translation products with defined specificity.

One reason for this specificity is the extreme conformational constraint on conotoxins due to the relatively abundant disulphide bonds. Conotoxin peptides contain between 20 and 50% cysteines, and most contain 3 disulphide bonds with a high density of disulfide crosslinking. Comparisons of the sequences of all known conotoxin peptides shows that, except for the conserved cysteines and a conserved glycine, the conotoxin residues show great variability and can be placed in three major categories (alpha, mu, and omega) based on cysteine residue groupings.

Of those that are highly crosslinked (or crossbridged), most belong to two groups, mu and omega, that have conserved primary frameworks as follows (C is Cys):

| | |
|---|---|
| mu | CC . . . . . C . . . . . C . . . . . CC; and |
| omega | C . . . . . C . . . . . CC . . . . . C . . . . . C |

The number of residues flanked by each pair of Cys residues varies from 2 to 6 in the peptides reported to date. The side chains of the residues that flank the Cys residues are apparently not conserved in peptides with different specificity, as in peptides from different species with similar or identical specificities. Thus, the conotoxins have exploited a conserved, densely crosslinked motif as a framework for hypervariable regions to produce a huge array of peptides with many different pharmacological effects. The mu and omega classes (with 6 Cys residues) have 15 possible combinations of disulfide bonds. Usually only one of these conformations is the active ("correct") form. The correct folding of the peptides may be directed by a conserved peptide that is cleaved from the N-terminus of the conopeptide to produce the small, mature bioactive peptides that appear in the venom.

With 2 to 6 variable residues between each pair of Cys residues, there are 125 ($5^3$) possible framework arrangements for the mu class (2,2,2, to 6,6,6), and 625 ($5^4$) possible for the omega class (2,2,2,2 to 6,6,6,6). Randomizing the identity of the residues within each framework produces $10^{10}$ to >$10^{30}$ peptides. "Cono-like" peptide libraries are constructed having a conserved disulfide framework, varied numbers of residues in each hypervariable region, and varied identity of those residues. Thus, a sequence for the structural framework for use in the present invention comprises Cys-Cys-Y-Cys-Y-Cys-Cys, or Cys-Y-Cys-Y-Cys-Cys-Y-Cys-Y-Cys, where Y is $(NNK)_x$ or $(NNS)_x$; N is A, C, G or T; K is G or T; S is G or C; and x is from 2 to 6. One can also use other codon strategies that result in subsets of amino acids (or codons) being specified in the library.

Because of the C-terminal location of the conotoxin peptides (when still part of their precursors) and the fact that disulphide bonds can form in the oxidizing environment of the periplasm, one may form one or more conformers of the peptide when using the signal sequence containing (periplasmic) fusion peptide vectors of the present invention. In some instances, there will be a favored conformation (matching or distinct from the wild-type conformation); in others, a variety of different conformations (due to a variety of disulphides forming among the 6 cysteines) will be formed. In the case where there is a favored conformation that is different from the wild-type conformation (for example, if the disulphides formed between adjacent cysteines as they enter the periplasm rather than the interlocking arrangement of the wild-type disulphides), one can reduce all of the disulphides and then reform them. This approach may allow the generation of a number of different conformations, depending on which disulphides are formed. The conformational diversity can be even greater with this system than others, given that there are 15 ways to arrange 6 cysteines in 3 disulphide bonds. In addition to providing the spatial arrangements of the cysteines that are found in nature, the present invention also provides novel arrangements of cysteines, including arrangements resulting in 2 or 4 instead of 3 disulphides and arrangements that vary the size of the loops between the disulphides.

Another family of compounds related to the conotoxins is the spider venom family. These peptides have motifs related to the double and triple interlocking disulphide bond format characteristic of the toxins and other proteins described above. In similar fashion, defensins are small polypeptides found in neutrophils and macrophages that have primarily an antimicrobial function, are likewise characterized by the presence of 6 cysteine residues, and are very rich in arginine. The present invention also provides scaffolding structures related to the spider venom and defensin scaffolding motifs.

Other specialized forms of structural constraints can also be used in the present invention. For example, certain serine proteases are inhibited by small proteins of conserved structure (e.g., pancreatic trypsin inhibitor). This conserved framework can incorporate degenerate regions as described herein to generate libraries for screening for novel protease inhibitors. Other changes can be introduced to provide residues that contribute to the peptide structure, around which the variable amino acids are encoded by the library members. For example, these residues can provide for alpha helices, a helix-turn-helix structure, four helix bundles, a beta-sheet, or other secondary or tertiary structural (framework or scaffolding) motifs.

As evidenced by the foregoing discussion, the available structural diversity for the present libraries is large. However, additional diversity can be introduced by a variety of means, such as chemical modification of the amino acids. For example, as one source of added diversity, a peptide library of the invention can be subjected to carboxy terminal amidation. Carboxy terminal amidation is necessary to the activity of many naturally occurring bioactive peptides. This modification occurs in vivo through cleavage of the N-C bond of a carboxy terminal Gly residue in a two-step reaction catalyzed by the enzymes peptidylglycine alpha-amidation monooxygenase (PAM) and hydroxyglycine aminotransferase (HGAT). See, Eipper et al., 1991, *J. Biol. Chem.* 266:7827–7833; Mizuno et al., 1986, *Biochem. Biophys. Res. Comm.* 137(3): 984–991; Murthy et al., 1986, *J. Biol. Chem.* 261(4): 1815–1822; Katopodis et al., 1990, *Biochemistry* 29:6115–6120; and Young and Tamburini, 1989, *J. Am. Chem. Soc.* 111:1933–1934, each of which is incorporated herein by reference.

Amidation can be performed by treatment with enzymes, such as PAM and HGAT, in vivo or in vitro. In a random peptide library of the present invention, amidation will occur on a library subset, i.e., those peptides having a carboxy terminal Gly. A library of peptides designed for amidation can be constructed by introducing a Gly codon at the end of the variable region domain of the library. After amidation, the library serves as a particularly efficient source of ligands for receptors that preferentially bind amidated peptides. Many of the C-terminus amidated bioactive peptides are processed from larger pro-hormones, where the amidated peptide is flanked at its C-terminus by the sequence -Gly-Lys-Arg-X (SEQ ID NO 6) . . . (where X is any amino acid). Oligonucleotides encoding the sequence -Gly-Lys-Arg-X-Stop can be placed at the 3' end of the variable oligonucleotide coding region. When expressed, the Gly-Lys-Arg-X is removed by in vivo or in vitro enzymatic treatment, and the peptide library is carboxy terminal amidated as described above.

Other modifications found in naturally occurring peptides and proteins can be introduced into the libraries to provide additional diversity and to contribute to a desired biological activity. For example, the variable region library can be provided with codons that code for amino acid residues involved in phosphorylation, glycosylation, sulfation, isoprenylation (or the addition of other lipids), etc. Modifications not catalyzed by naturally occurring enzymes can be introduced by chemical means (under relatively mild conditions) or through the action of, e.g., catalytic antibodies and the like. In most cases, an efficient strategy for library construction involves specifying the enzyme (or chemical) substrate recognition site within or adjacent to the variable nucleotide region of the library so that most members of the library are modified. The substrate recognition site added can be simply a single residue (e.g., serine for phosphorylation) or a complex consensus sequence, as desired.

Figure 2:
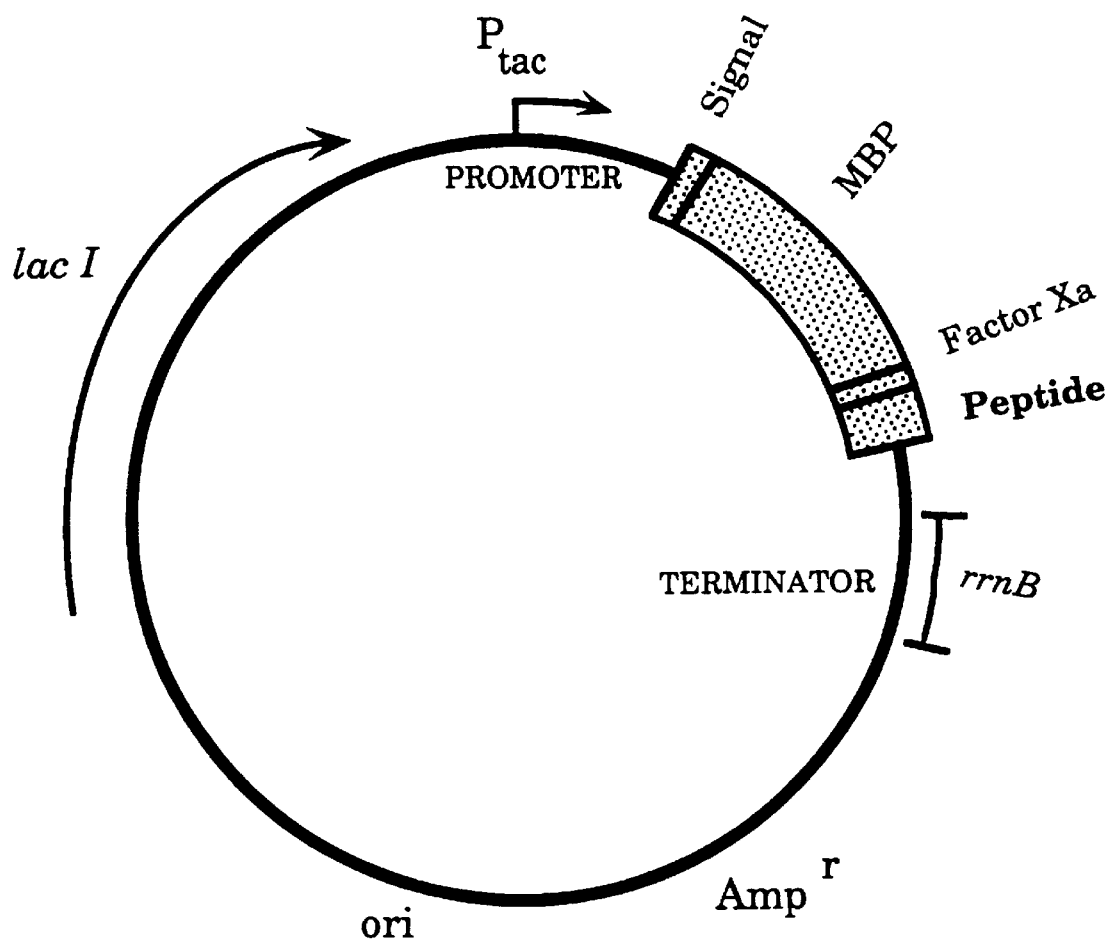
FIG. 2 shows a function map of plasmid pMalPΔNde.

Just as one can vary the random peptide coding sequence of the present expression vectors to obtain desired properties or reactivities, so too can one vary other regions of the expression vector. An illustrative MBP-random peptide expression vector of the invention is shown in FIG. 2. In bacterial host cells, the expression of the fusion protein occurs in the cytoplasm of the host cell, but one can target the fusion protein to the periplasm by appropriate choice of signal sequences incorporated into the vector. The site of deposition is determined by the presence or absence of a signal peptide in the amino terminus of the chimeric fusion protein. In the case of the MBP vector, a deletion between amino acids 2 and 26 of the MBP coding sequence removes the signal sequence and results in cytoplasmic localization—the retention of this same motif results in periplasmic localization. Thus, although many different versions of the MBP carrier protein can be employed in the method of the present invention, two particular versions are preferred. In the first version, the MBP carrier protein portion of the fusion protein is expressed with the MBP gene signal sequence that directs the fusion protein to the periplasm. The second version involves the deletion of certain N-terminal amino acids of MBP, noted above, which deletion abolishes signal integrity and results in cytoplasmic accumulation of the fusion protein.

Those of skill in the art recognize that any of a large number of signal peptide encoding DNA sequences can be used in the expression vectors of the present invention for purposes of targetting the fusion protein to the periplasm of the host cell. The choice of site for protein deposition depends on a number of criteria. In terms of ease of purification, the periplasmic protein can be isolated from most other cellular proteins by a simple osmotic shock, while the isolation of the cytoplasmic protein requires disruption of the cells. In terms of total protein yield, cytoplasmic deposition results in approximately 5 to 10 times more fusion protein (~30% of total protein present is the fusion protein versus ~5% of the total protein present using the periplasmic vector). In both cases, large amounts of the peptide fusion can be isolated (~100 mg/liter of culture for cytoplasmic and ~10 mg/liter of culture for periplasmic). In terms of protein processing, proteins exported to the periplasm can undergo disulphide bond formation while those in the cytoplasm retain their cysteines in the reduced form. The choice of site of deposition of the protein depends on the specific application.

Another important feature of the recombinant vectors of the present invention is the promoter and other transcription/translation control sequences for the fusion protein coding sequence. Preferred control sequences for the expression of the fusion proteins encoded by the recombinant DNA expression vectors of the invention are the $P_{tac}$ promoter (a trp/lac synthetic promoter), the rrnB terminator, and translation signals from the MBP gene. One can also use an inducible promoter, such as any of the promoters selected from the group consisting of the araB, lambda pL, (which can be either nalidixic acid or heat inducible or both), trp, lac, T7, T3, and trc (another trp/lac hybrid) promoters to control fusion protein number. A regulated promoter is also useful to limit the amount of time that the peptide ligands are exposed to cellular proteases. By inducing the promoter a short time before lysing the cells containing a library, one can minimize the time during which proteases can act on the fusion protein.

The araB promoter is an inducible promoter that normally drives expression of the enzymes of the *E. coli* araBAD operon, which are involved in the catabolism of L-arabinose. The araB promoter is regulated both positively and negatively, depending on the presence of L-arabinose in the growth medium, by the AraC protein. This promoter can be catabolite repressed by adding glucose to the growth medium and induced by adding L-arabinose to the medium. The araB promoter is also regulated by the CAP protein, an activator involved in the *E. coli* system of catabolite repression.

To prevent overproduction of the fusion protein encoded by any vector of the present invention that has an inducible promoter, one can grow the transformants first under non-producing conditions (to minimize exposure of the fusion protein to cellular proteases and to minimize exposure of the cell to the possibly deleterious effects of the fusion protein) and then under inducing or "partially inducing" conditions. For the araB promoter, partial induction can be achieved with as little as $3.3 \times 10^{-5}\%$ of L-arabinose (as demonstrated by increased repression in the assay described below). A preferred way to achieve partial induction consists of growing the cells in 0.1% glucose until about 30 min. before the cells are harvested; then, 0.2 to 0.5% L-arabinose is added to the culture to induce expression of the fusion protein.

Once the library is constructed, host cells are transformed with the library vectors. The successful transformants are typically selected by growth in a selective medium or under selective conditions, e.g., an appropriate antibiotic, which, in the case of plasmid pMalP and pMalC (see Example 1) derivatives, is ampicillin. This selection may be done on solid or in liquid growth medium. For growth on solid medium, the cells are grown at a high density (~$10^8$ to $10^9$ transformants per $m^2$) on a large surface of, for example, L-agar, containing the selective antibiotic to form essentially a very dense collection of individually identifiable colonies. For growth in liquid culture, cells may be grown in L-broth or LB broth (10 g of tryptone, 5 g of NaCl, and 5 g of yeast extract per liter) and antibiotic through about 10 or more doublings.

One can use host cell bacterial strains deficient in particular peptidases to avoid the problem of unwanted proteolytic degradation of the random peptide fusion protein. In the case of cytoplasm targetted peptide fusions, the use of the *E. coli* protease mutants lon or htpR may reduce degradation (see Gottesman, 1989, *Ann. Rev. Genet.* 23: 163–198, incorporated herein by reference). To avoid degradation in the periplasm, the use of the deqP mutant (see Strauch and Beckwith, 1988, *Proc. Natl. Acad. Sci. USA* 85:1576–1580, and Strauch et al., 1989, *J. Bacteriol.* 171:2689–2696, each of which is incorporated herein by reference) may be helpful. The mutant ompT, a protease known to be active during the preparation of cell extracts (see Riggs, 1990, supra), may be useful for either the cytoplasm or periplasm targetted peptide fusion proteins. Another mutation known to reduce proteolysis is clpA,P. Preferred *E. coli* strains for purposes of the present invention include MC1061 (araD139 Δ(araABC-leu)7696 thr ΔlacX74 qalU qalK hsdR mcrB rpsL(strΔ) thi) and *E. coli* B strain ARI 161 (lon-11, sulA1, hsdR17, Δ(ompT-fepC), ΔclpA319::kan). ARI 161 is a protease deficient strain and serves to minimize proteolysis of the peptides in the library, which reduces the available diversity.

Once host cells have been selected and transformed with the random peptide fusion protein expression vectors of the invention, one will generally screen the library for peptides that can bind to a receptor. The peptide library produced by the present method is especially useful in screening for ligands that bind to a receptor of interest. As noted above, efficient peptide screening systems often provide a direct relationship between the presented peptide and the genetic information that encodes the peptide presented. The methods of the invention provide three different approaches that provide an analogous direct relationship between the tripartite fusion protein of the invention and the genetic material that encodes the fusion protein.

In general, however, each of these methods comprises the steps of: (a) placing the transformed host cells of the peptide library on a surface such that each different transformant is located on said surface at a location different from the location of the other different transformants; (b) rendering the fusion proteins present in said transformed host cells on said surface prepared in step (a) accessible for receptor binding by osmotic shock or lysis of said transformed host cells; (c) contacting the fusion proteins rendered accessible in step (b) with a labelled receptor under conditions conducive to specific peptide—receptor binding; and (d) identifying transformants that produce fusion proteins with peptides that bind to the receptor by determining the location of said labeled receptor on said surface. Those of skill in the art recognize that the receptor need not be labeled directly; for instance, one could bind unlabeled receptor to the fusion proteins and then label the receptor with a labeled anti-receptor antibody.

Figure 3:
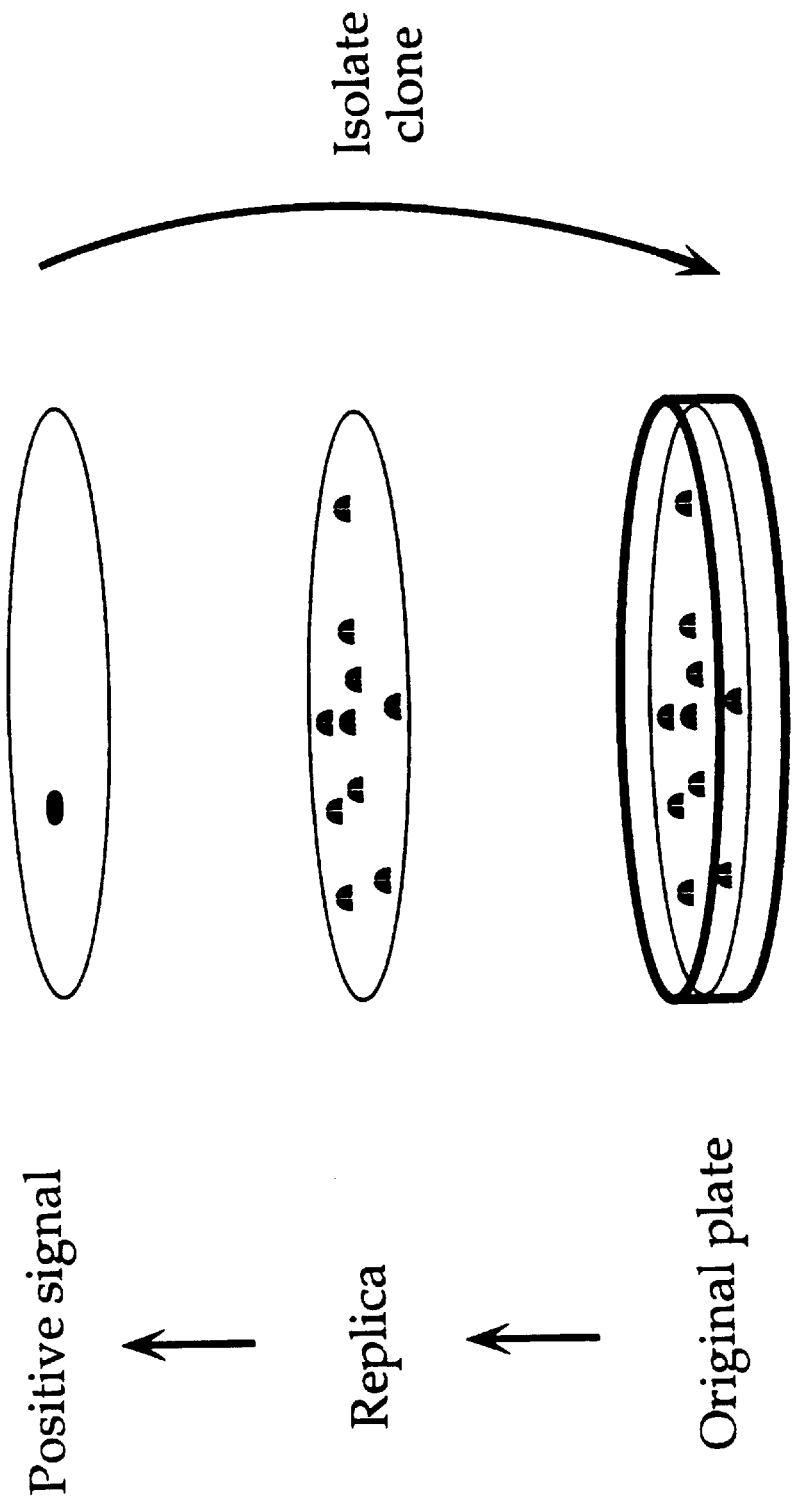
FIG. 3 shows a method for replicating bacterial transformants to aid in the identification of a ligand that binds to a receptor of interest.

In one embodiment, the screening method can be carried out in a Benton and Davis type screening format, in which the library of clones is plated out on nitrocellulose membrane filters (placed on nutrient agar plates), and then replica filters of the library of clones are prepared, as shown in FIG. 3. One of the filter copies is then treated to allow cell lysis and protein immobilization for the presentation of the peptide fusions; the other filter copy allows the propagation of the sister colonies of any positive clones. Basically, master and replica filters are made (10,000–100,000 colonies per filter, although one can plate as many as 10,000,000 recombinants on a single nine cm plate), and one of the filters is chloroform treated to lyse the cells, detergent treated to solubilize the membranes, and DNAseI treated to digest the genomic DNA. The filter is then 'blocked' by either gelatin, milk, or BSA, and then treated with an appropriately labelled receptor (whether it be an enzyme, a cell-surface receptor, a nucleic acid, or an antibody; see Young and Davis, 1983, *Proc. Natl. Acad. Sci. USA* 80: 1194–1198, and *Science* 222: 778–782, each of which is incorporated herein by reference).

The second approach, which is less tedious, relies on two distinct features of the peptide fusion protein system: (1) the peptide fusions can be exported to the periplasm where they can be released from the cells with a mild osmotic shock; and (2) the carrier moiety of the fusion protein allows the immobilization of the fusion protein on a solid support of amylose. A single copy of all the colonies on a filter will suffice—the filter with the colonies is osmotically shocked in situ and placed in contact with amylose paper. The specifically adsorbed fusion proteins can then be probed with the receptor, and the corresponding viable colonies on the original filter can be propagated.

The third approach involves the propagation of the recombinant plasmids in a host cell that is lysogenic for a temperature sensitive lambda prophage. This approach involves the induced expression of the fusion protein followed by increasing the temperature to cause the cell to enter the lytic phage cycle, which ends with lysis of the cell. The proteins are released biologically, and if cytoplasm directed vectors are used, then approximately ten-fold more fusion protein (as compared to periplasm directed vectors) is produced. The method provides increased sensitivity and offers the opportunity to plate out more bacterial colonies, because smaller colonies can be detected. Not all of the cells will enter the lytic phase, so there is no need to produce a replica copy of the library. Vectors encoding lead compounds can be rescued by going back to the original agar plates from which the lysed colonies were lifted onto the nitrocellulose membrane filters for screening. Included in this aspect of the invention is the related technique of coexpressing with the periplasm directed fusion protein of interest a phage or viral protein that causes the host cell outer membrane to be permeable to the fusion protein (i.e., the N-terminal portion of the pIII gene product has this effect).

The conservative number of colonies that can be reasonably screened is about 40,000 colonies per plate with 50 plates, about $2 \times 10^6$ independent clones. If $1 \times 10^6$ colonies are immobilized per plate and 100 filters processed, then $1 \times 10^8$ clones can be screened. Another advantage of solid-phase screening relates to the ease with which one can determine the percentage of individual recombinants in the library that share a desired trait, important for the statistical analysis of the screening. Coupled with knowlege of the distribution of peptides in the total library, the number of lead compounds identified contains much information about the specific requirements for binding. A receptor that can bind a number of ligands is readily distinguishable from a receptor that can bind only a few ligands with the method of the present invention, and the invention provides results statistically addressable in terms of SAR.

Receptor-ligand interactions will generally be determined by first forming immobilized complexes comprising fusion protein or random peptide bound specifically to a receptor and then separating nonspecifically binding materials, which are washed away. A variety of washing procedures can be used to enrich for retention of molecules with desired affinity ranges. For affinity enrichment, a certain number of library equivalents (a library equivalent is a complete set of each recombinant fusion protein in a library, so $10^4$ equivalents of a library of $10^9$ members is $10^{13}$ compounds) are incubated with a receptor. The receptor can be in any of several different forms appropriate for the particular binding assay employed. In one example, the receptor is labeled (either directly or via a labeled anti-receptor antibody) and in solution, and the immobilized library is screened with the soluble receptor.

Of course, further studies of an individual library member can be facilitated by utilizing immobilized receptor, with the receptor immobilized directly or via a second, non-blocking ligand, with appropriate spacer or linker moieties optionally employed. For instance, the second ligand can be biotin or a non-blocking anti-receptor antibody. The receptor, so modified, is incubated with the library member, and binding either occurs with both reactants in solution or after immobilization of the receptor. The resulting complexes can be bound to streptavidin (or avidin) through the biotin moiety. The streptavidin may be immobilized on a surface such as a plastic plate or on particles, in which case the complexes are physically retained. In addition, any of the reagents may be labelled, with a fluorophore, for example, to tag the active fusion protein for detection and/or isolation by sorting procedures, e.g., on a fluorescence-activated cell sorter.

Fusion proteins with random peptides without the desired specificity can be prevented from appearing to react specifically with a receptor by washing after the receptor binding step. The degree and stringency of washing required will be determined for each receptor/peptide of interest. A certain degree of control can be exerted over the binding characteristics of the peptides identified by adjusting the conditions of the binding reaction and the subsequent washing. The temperature, pH, ionic strength, divalent cation concentration, and the volume and duration of the washing will select for peptides within particular ranges of affinity for the receptor. Selection based on slow dissociation rate, which is usually predictive of high affinity, is the most practical route. This may be done either by continued incubation in the presence of a saturating amount of free ligand, or by increasing the volume, number, and length of the washes. In each case, the rebinding of dissociated peptide-receptor can be prevented, and receptor-ligand pairs with higher affinity can be recovered. Additional modifications of the binding and washing procedures can be applied to find peptides that bind receptors under special conditions.

Although the screening method can be highly specific, the procedure does not have to discriminate between peptides of modest affinity (e.g. micromolar dissociation constants) and those of high affinity (e.g. nanomolar dissociation constants or greater) in all embodiments. The ability to select peptides with relatively low affinity can result from multivalent interaction between a fusion protein and a receptor. Multivalent interaction can produce a high avidity and tenacious adherence of the fusion protein during washing. To enrich for the highest affinity peptide ligands, a substantially monovalent interaction between fusion protein and the receptor is appropriate. One advantage of the present invention arises from the production of monovalent fusion protein. If one utilizes a multivalent receptor, such as an antibody, then one can still obtain monovalent interaction by immobilizing the fusion protein at very low density.

A strategy employing a combination of conditions favoring multivalent or monovalent interactions can be used to advantage in identifying new peptide ligands for receptor molecules. By conducting screening under conditions that promote multivalent interactions, one may be able to identify relatively low affinity ligands. One can then use high stringency washing to identify high affinity ligands. Multimerization of the receptor, via e.g. antibodies or crosslinking, may be helpful at this stage. The high avidity (low affinity) step may select a large pool or peptides with a wide range of affinities, including those with relatively low affinity. Subsequent screening under conditions favoring increasingly monovalent interactions and a slow dissociation rate may then allow the identification of the highest affinity peptides.

One can also determine the relative affinity of a series of related peptide ligands by measuring the dissociation rate for a peptide of interest and the selected receptor molecule under substantially monovalent conditions. For example, one can measure the dissociation of a Fab fragment from immobilized fusion protein-receptor complexes. This procedure avoids the necessity and inconvenience of separately determining binding affinities for each peptide, which could be especially burdensome if a large number of peptides have been selected.

Another advantage of the present invention relates to the ease of purification of peptides of interest using the reagents and methods of the invention. Peptides with desired binding properties can be isolated from the transformants identified as of interest by isolating the fusion protein produced by the transformant via immobilization on a solid support through a specific carrier protein/support group interaction and by cleaving the peptide from the fusion protein by treatment with a protease specific for the proteolytic cleavage site in the fusion protein.

Figure 4A:
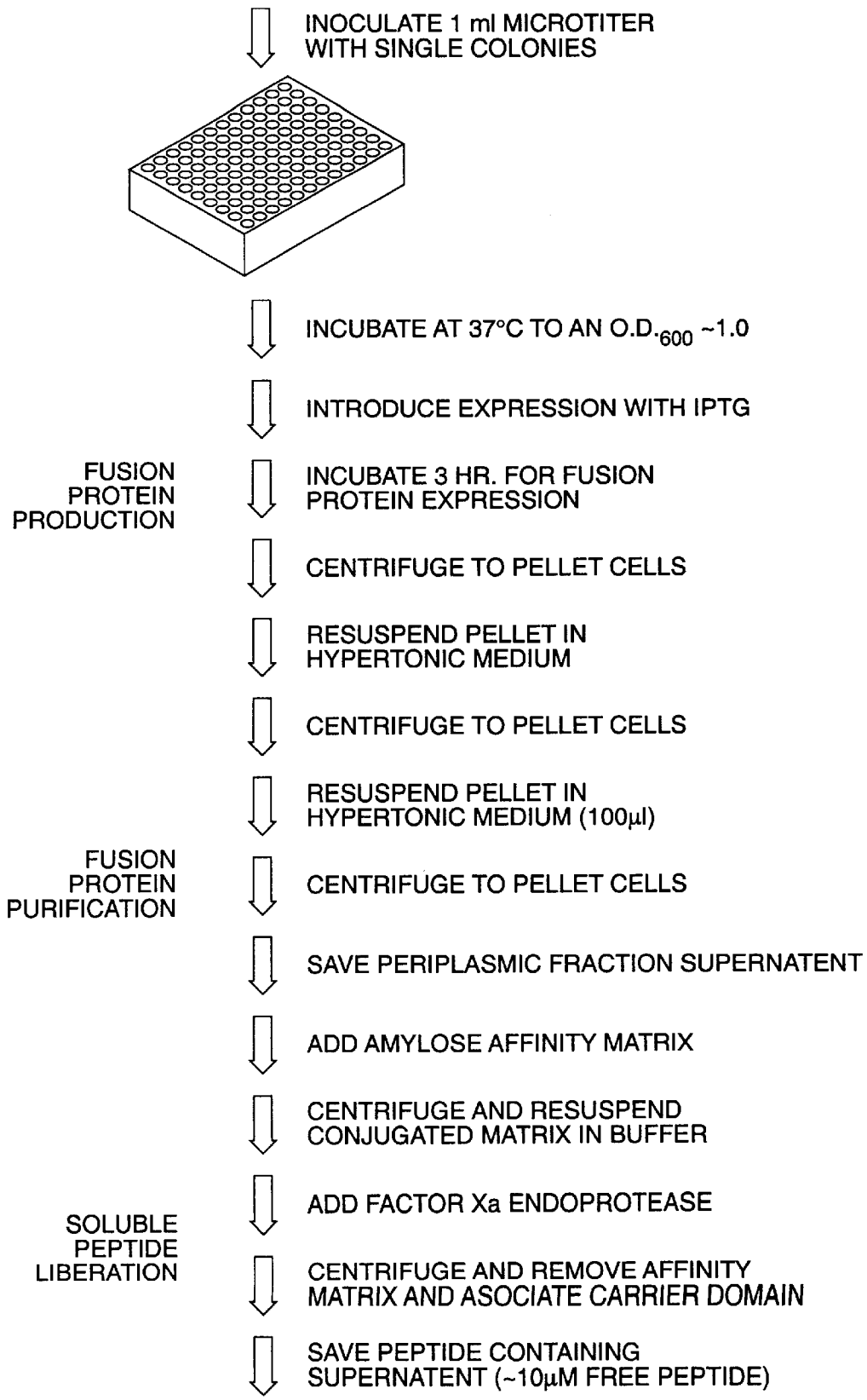
FIGS. 4A and 4B, shows how the present invention can be used either to isolate small amounts of a large number of different random peptides or large amounts of a small number of random peptides.
Figure 4B:
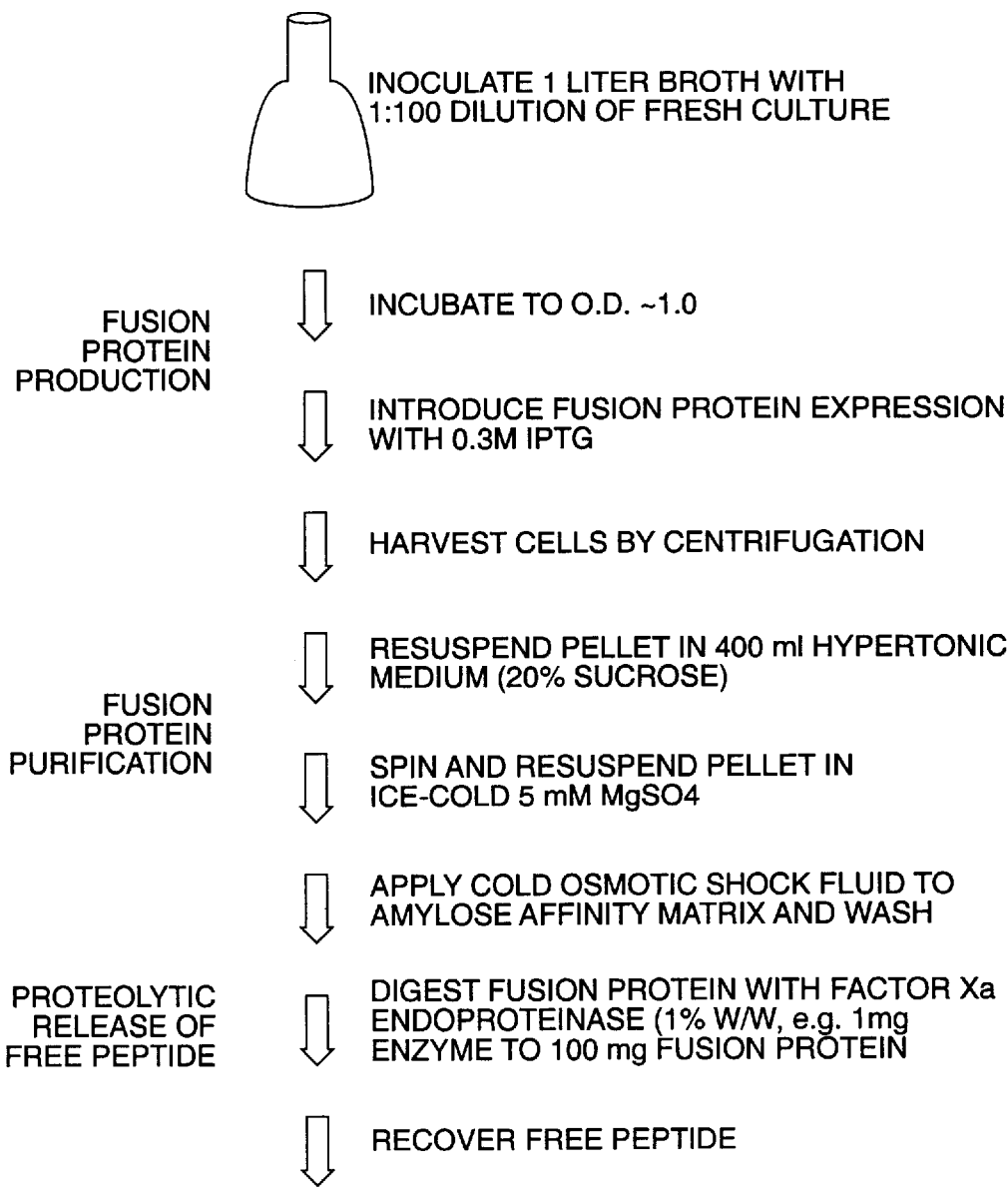

Given the high level of expression of periplasm targetted fusion proteins of the present invention, one has an ideal system for the production of thousands of different soluble peptides, as shown in FIG. 4A. The key elements of this system are microtiter plates (96 samples per plate) and automated equipment (for instance, Beckman's Biomek 1000) for all of the sample handling except plate centrifugation. This procedure allows for the production of microgram quantities of free soluble peptides at micromolar concentrations, sufficient for first generation pharmacological studies. The present invention can also be used to produce milligram quantities of a peptide, as shown in FIG. 4B. Depending on the quantity and the purity required for the subsequent pharmacologic analyses, the methods provided by the present invention can be more cost effective than solid phase chemical processes.

Automation makes the present invention suited to many different applications, for instance, comparing receptor binding results between large numbers of fusion protein displayed peptides and free soluble counterparts of the fusion protein displayed peptides. Such information will be useful in SAR analysis to determine which sequences are important for binding. In similar fashion, the methods and reagents of the present invention can be used to analyze leads generated by other systems, such as the system described by Cull et al., March 1992, *Proc. Natl. Acad. Sci. USA* 89:1815–1869 and Cwirla et al., supra. If the lead compound was generated from a system in which the peptides are presented with a free amino terminus, then one could use an embodiment of the present invention in which the chimeric peptide fusion protein presents the random peptide with a free carboxy terminus. Such an approach would show whether a free amino or carboxy terminus or an internal feature of the presented peptide is an important feature of the molecular recognition element responsible for binding peptide to receptor. Although many embodiments of the present invention result in the generation of a tripartite fusion protein with the random peptide at the carboxy terminal end of the fusion protein, the present invention can also be used to present random peptides at the amino terminal end of a carrier protein, such as MBP.

Thus, the present invention can be used to construct peptide ligands of great diversity. The random peptides of the present libraries can be displayed with a free carboxy terminus, or a free amino terminus, or internal to the carrier protein, and so add diversity to the peptide structures available for receptor binding. The presentation of peptide ligands at the carboxy terminus also facilitates amidation and ensures that stop codons in the degenerate region shorten rather than destroy individual clones. The presence of stop codons in the random peptide coding sequence actually serves to create additional diversity, by creating peptides of differing lengths. The fusion proteins of the invention also allow the display of potential ligands with a wide range of sizes. In addition, these fusion proteins can be cytoplasmic or periplasmic proteins, unlike the phage fusions, which are exported to the periplasm. The availability of both cytoplasm and periplasm targetted fusion proteins increases the total available peptide diversity, because the two types of libraries are exposed to different cellular compartments and so are exposed to different sets of *E. coli* proteases and to different reduction/oxidation environments.

Libraries of peptides produced and screened according to the present invention can be used to map antibody epitopes. The ability to sample a large number of potential epitopes has clear advantages over certain chemical synthesis methods now in use and described in, among others, Geysen et al., 1987, *J. Immunol. Meth.* 102:259–274. In addition, these libraries are useful in providing new ligands for important binding molecules, such as hormone receptors, adhesion molecules, enzymes, and the like.

The present libraries can be generalized to allow the screening of a wide variety of peptide and protein ligands. In addition, the vectors are constructed so that screening of other ligands encoded by the plasmid is possible. Another application of the present method involves the use of a modified version of the vector to isolate genes whose products modify peptides, proteins, or RNA in a desired fashion. This application requires the availability of a receptor that binds specifically to the modified product. As can be appreciated from the disclosure above, the present invention has a wide variety of applications. Accordingly, the following examples are offered by way of illustration, not by way of limitation.

EXAMPLE 1

Construction of Plasmids pMalPΔNde and pMalCΔNde

Plasmids that drive expression of maltose binding protein (MBP) are commercially available but contain an NdeI restriction enzyme recognition site near the origin of replication that can be removed to facilitate construction of the vectors of the invention. This example describes the construction of plasmids that encode MBP and lack an NdeI site.

Plasmids pMalP and pMalC were purchased from New England Biolabs, Inc. (Beverly, Mass). These plasmids differ in the amount of MBP signal peptide encoded by the plasmid ("P" is periplasm directed; "C" is cytoplasm directed). The plasmids also encode the lacZ alpha fragment with a multiple cloning site under the control of the lac promoter.

About 15 μg of each plasmid were individually digested to completion with restriction enzyme NdeI and then treated with mung bean nuclease to remove the single-stranded extensions resulting from the digestion. Each NdeI-digested plasmid was then self-ligated under dilute concentrations (100 ng/10μl), and the ligated DNA was used to transform *E. coli* host cells. The transformants were selected on ampicillin-containing plates that also contained IPTG and X-Gal, and ampicillin resistant, blue colored colonies were selected, cultured, and used as a source of plasmid DNA.

Derivatives of both pMalc and pMalP that lacked the NdeI site were isolated in this manner and designated, respectively, pMalCΔNde and pMalPΔNde. A restriction site and function map of plasmid pMalPΔNde is shown in FIG. 2.

EXAMPLE 2
Construction of a Dynorphin B Misincorporation Library

This example illustrates how the methods and reagents of the invention can be used to generate diversity around a "lead" peptide and to find peptides related in sequence to, but different from, the lead peptide with respect to affinity for a specific receptor. In this example, the lead peptide is dynorphin B.

To construct a positive control vector, plasmid pMal-CΔNde was modified to code for the expression of a fusion protein composed of MBP, a factor Xa cleavage site, and dynorphin B. Plasmid pMalCΔNde was digested with restriction enzymes BamHI and HindIII, and the digested DNA was ligated to a synthetic double-stranded nucleic acid composed of single-stranded nucleotides ON-269 and ON-270. These oligonucleotides are shown below in duplex form.

(SEQ ID NO 7)
ON-269 5'-GATCCATCGAGGGTCGTTACGGTGGTTTCCTGCGTCGT- (SEQ ID NO 8)
ON-270       GTAGCTCCCAGCAATGCCACCAAAGGACGCAGCA-

ON-269 -CAGTTCAAAGTTGTTACCTAAA-3'

ON-270 -GTCAAGTTGCAACAATGGATTTTCGA-5'

Oligonucleotides ON-269 and ON-270 and the BamHI-HindIII-digested plasmid pMalCΔNde were ligated together, and the ligated DNA was used to transform *E. coli* cells to ampicillin resistance. Several ampicillin resistant colonies were selected and screened for plasmid DNA of the desired structure. The desired plasmid was isolated and designated pMalCΔNdeDynB.

To construct the misincorporation library, the BamHI-HindIII-digested plasmid pMalCΔNde was ligated to a synthetic double-stranded nucleic acid composed of single-stranded oligonucleotides ON-271, ON-272, and ON-273. These oligonucleotides are shown below in duplex form; the lower case letters in the sequence shown for oligonucleotide ON-271 indicate positions at which misincorporation was designed to occur.

The misincorporation strategy was carried out by using 70/10/10/10 mixtures of nucleoside triphosphates, such that the mixture contained 70% of the nucleoside triphosphate indicated by the lower case letter in the sequence and 10% each of the remaining three nucleoside triphosphates.

Oligonucleotides ON-271 (0.33 μg), ON-272 (0.06 μg), and ON-273 (0.09 μg) and the BamHI-HindIII-digested plasmid pMalCΔNde (3 μg) were ligated together, and the ligated DNA was used to transform *E. coli*. The transformants were plated either directly on agar plates (e.g. 1.5% bactoagar in LB medium) or onto nitrocellulose filter discs (e.g. Biorad 0.45 mm pore nitrocellulose) placed on agar plates, and then incubated at 30° C. for ~16 hours, resulting in colonies with a diameter of ~0.1–0.5 mm. A replica filter was made by lifting portions of each colony onto a second nitrocellulose filter from either the plate or the first filter, resulting in a mirror image exact replica. The replicas were incubated for ~3 hrs at 37° C. on plates containing the inducer (0.4 mM IPTG).

To lyse the cells and expose the fusion protein for receptor screening, the IPTG-induced replica filters were first exposed to chloroform vapors for ~15 minutes to facilitate membrane solubilization. Individual filters were placed on water-saturated paper towels and exposed to chloroform vapors in an enclosed container containing an open dish of chloroform. Filters were then incubated for about 16 hours at room temperature in a solution containing lysozyme to digest the bacterial cell wall and DNAseI to digest the bacterial genome (the lysozyme (at 40 mg/ml) and DNAseI (at 1 mg/ml) were stabilized in a solution consisting of 100 mM Tris at pH 7.8; 150 mM NaCl; 5 mM MgCl$_2$; and 1.5% bovine serum albumin). The filters were then extensively washed (four times for twenty minutes each) in a solution consisting of 10 mM Tris at pH 8.0; 150 mM NaCl; and 0.05% Tween 20 (TNT).

For screening with the antibody, the filters were blocked against non-specific probe binding by incubation in a solution of 3% non-fat dry milk (Carnation) in 1× PBS (Dulbecco's phosphate buffered saline) from one to sixteen hours. The filters were then reacted with anti-Dynorphin B peptide mouse monoclonal antibody (see Barrett and Goldstein, 1988) at a concentration of about one μg/ml in 10 mM Na phosphate, pH 7.0, at 4° C. overnight. Filters were washed in 1× PBS containing 0.05% Tween 20 three times for 20 minutes each and then blocked again, this time with 0.3% milk in PBS for ½ hr. Goat anti-mouse monoclonal labelled with alkaline phosphatase (Pierce) diluted 1:4000 in 0.3% milk in PBS was then added to the filters, which were then incubated for 2 hours at room temperature and then again washed with PBS/Tween 3 times for 20 minutes each wash. Antibody-specific clones were then detected by adding the alkaline phosphatase substrate mixture of BCIP (5-bromo-4-chloro-3-indolyl phosphate) and NBT (nitroblue tetrazolium; purchased from Biorad).

Clones were divided into three catagories depending upon the intensity (faint, average, intense) of the blue/purple product of the enzyme. Individual clones were isolated by identifying the corresponding clone (or clone region) on the ON-271 5'-GATCCATCGAGGGTCGTtacggtggtttcctgcgtcgtcagttcaaa-

ON-272      3'-GTAGCTCCCAGCA-5'                              (SEQ ID NO 9)

ON-271 -gttgttaccTAAGGAGCACTGCA-3'                           (SEQ ID NO 10)

ON-273      3'-ATTCCTCGTGACGTTCGA-5'                         (SEQ ID NO 11)

master plate and purifying the desired clone by subsequent rounds of bacterial plating and filter screening as above. Plasmid DNA for clone sequencing the clone was prepared by the standard alkaline lysis 'Iminipre' method (e.g. Sambrook et al., 1989). Double-stranded sequencing (Chen and Seeburg, 1985) of the peptide-encoding DNA insert utilized a sequencing primer (5'-GGTCGTCAGACTGTGCATGAAGCC-3') (SEQ ID NO 12) located 48 bp from the insert site in the MBP gene.

Fusion protein production was accomplished by growing a small culture (~50 mL) of the clone of interest to log phase ($OD_{600}$ of ~0.5) and inducing the production of the MBP fusion protein with IPTG (0.5 mM) and incubating the culture for a further 3 hours (final $OD_{600}$ of ~3.0). The cells were then centrifuged into a pellet (4000 ×G; 10 minutes) and resuspended in 2.5 mL of lysis buffer (10 mM phosphate pH 7; 30 mM NaCl; 0.25% Tween 20; 10 mM beta-mercaptoethanol; 10 mM EDTA; and 10 mM EGTA). Cell lysis was by repeated freezing and thawing (5 times alternating liquid nitrogen and 37° C. water) and sonication (3 times for 1 minute each, Branson, setting 7, tubes on ice). Following the addition of NaCl to 0.5 M and a high speed centrifugation (10,000×G, 30 minutes), the supernatant was mixed 1:5 with column buffer (10 mM phosphate pH 7; 0.5 M NaCl; 1 mM Na azide; 10 mM beta-mercaptoethanol; and 1 mM EGTA) and passed over a 2 mL amylose (New England Biolabs) chromatography column (Biorad) pre-equilibrated with column buffer. After loading with cell extract, the column was washed with 3 column volumes of column buffer with 0.25% Tween 20 and then 5 column volumes of column buffer without Tween. The fusion proteins were eluted from the column with column buffer containing 10 mM maltose. Fusion proteins were characterized by polyacrylamide gel electrophoresis and western blot analysis with the anti-dynorphin B monoclonal.

Figure 7:
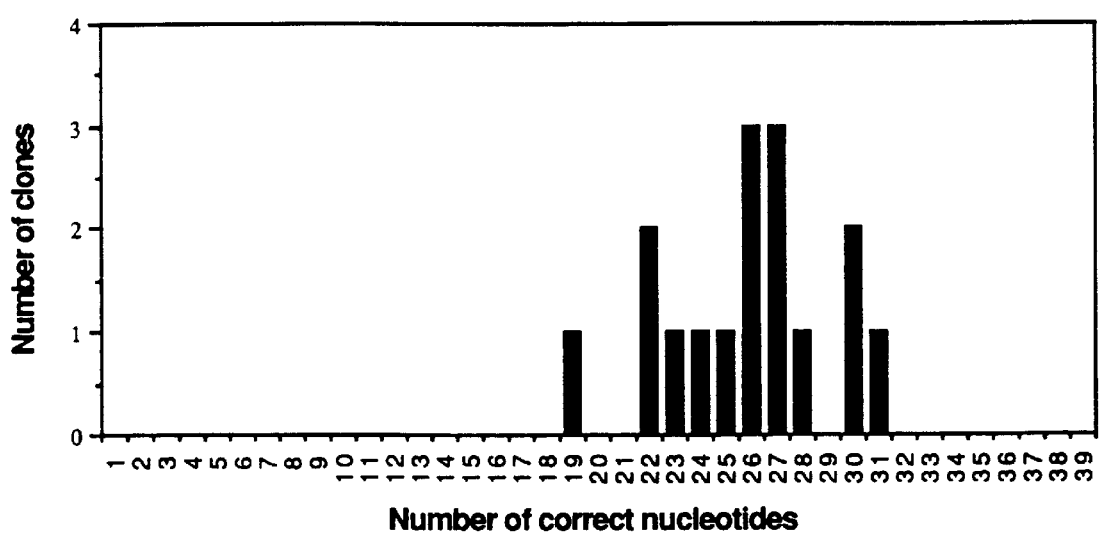
FIG. 7 shows the misincorporation frequency observed in the 16 different recombinants described in FIG. 5.

The nucleotide sequence for the peptides in 16 randomly chosen members of the 70/10/10/10 dynorphin B library is shown in FIG. 5. Only differences in sequence from the starting sequence are listed. Deduced amino acid sequences of the same clones are shown in FIG. 6. The pound signs (#) in FIG. 6 indicate the presence of a stop codon at the position indicated in the peptide coding sequence. No bias in nucleotide misincorporation frequency was detected. The expected 30% error rate was observed both in the individual peptide sequences and at the same nucleotide position in the group of sequences (see FIG. 7).

Figure 8A:
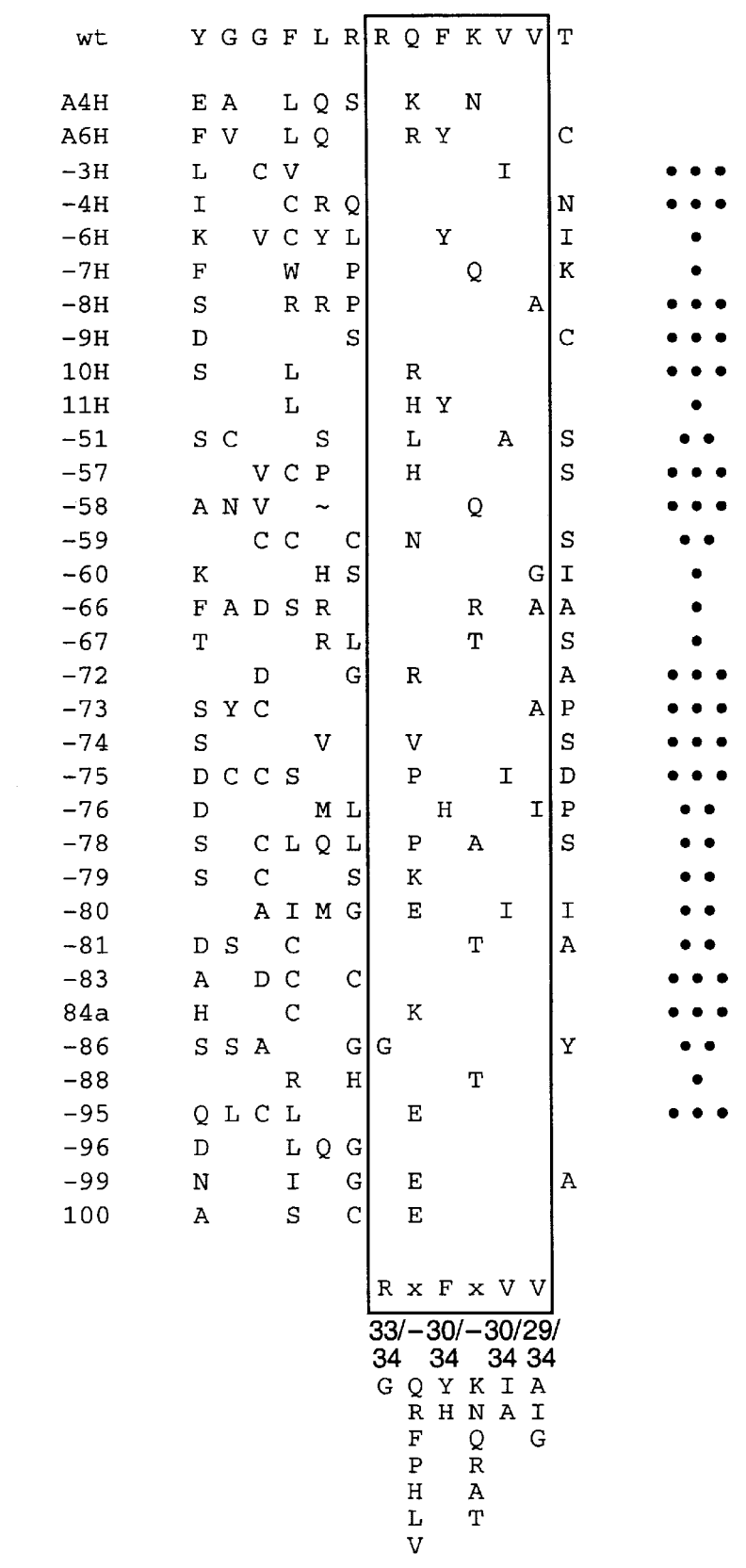
Figure 8B:
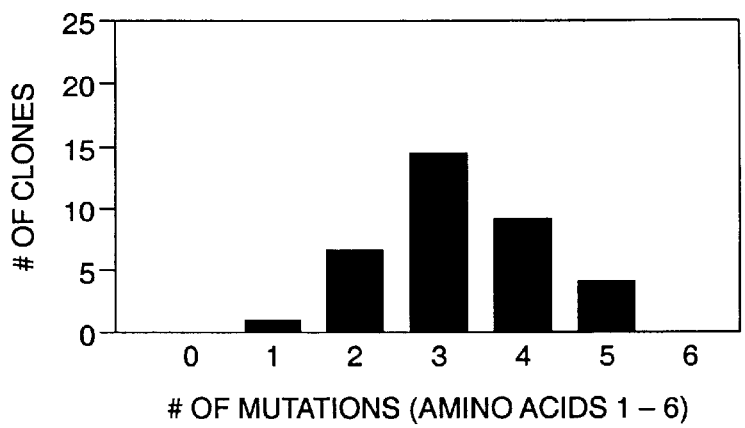
FIG. 8 shows the amino acid sequence encoded by anti-dynorphin B antibody positive fusion proteins produced by the dynorphin B misincorporation library.
Figure 8C:
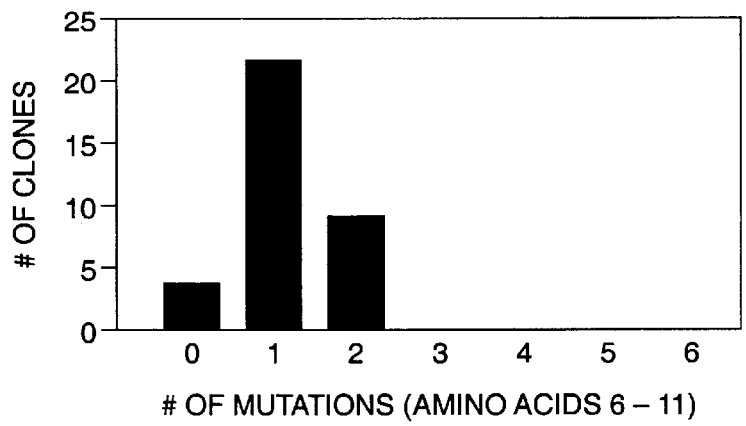
Figure 9A:
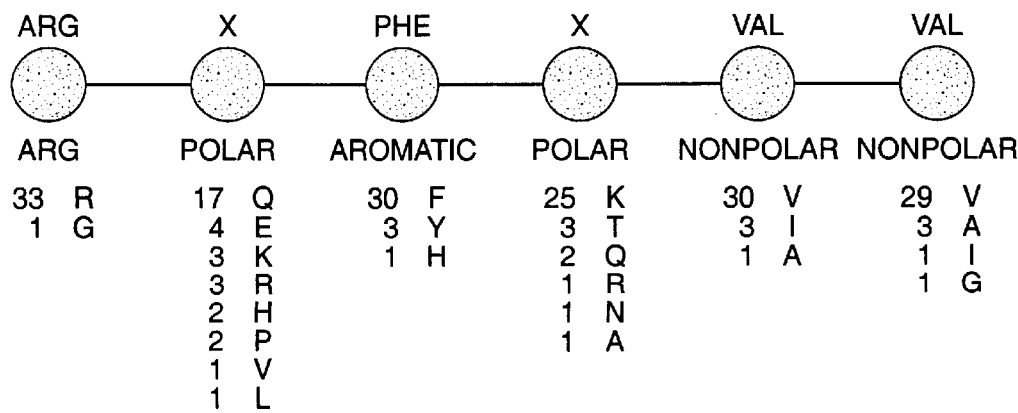
FIG. 9 shows a summary of the fusion proteins produced by the dynorphin B misincorporation library that retain the ability to bind to anti-dynorphin B antibody.
Figure 9B:
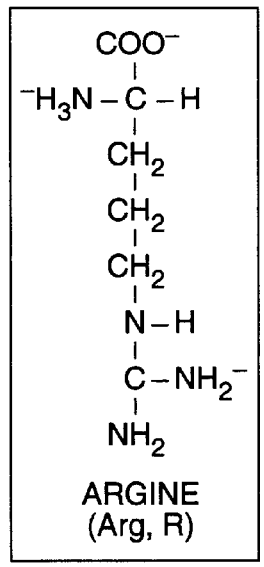
Figure 9C:
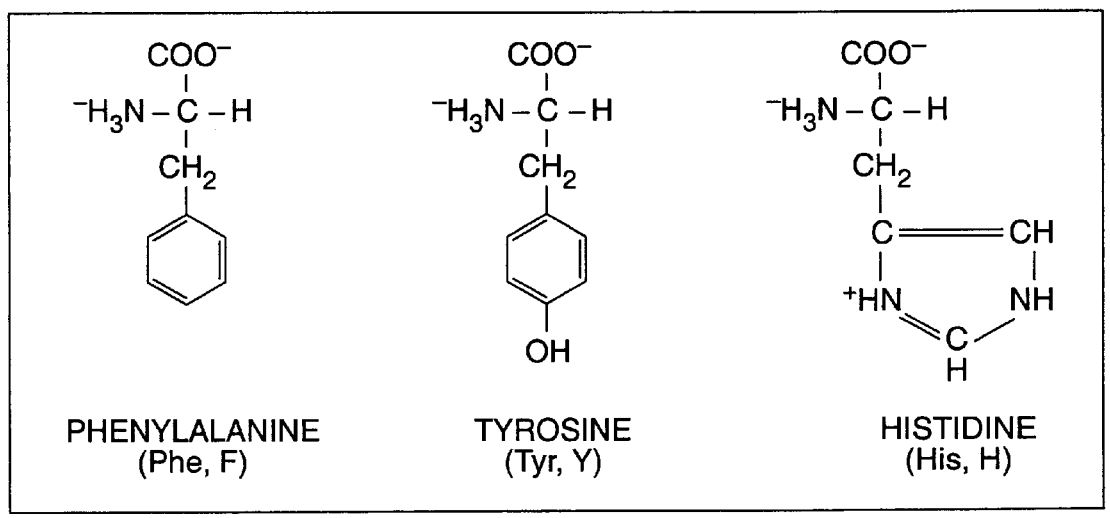
Figure 9D:
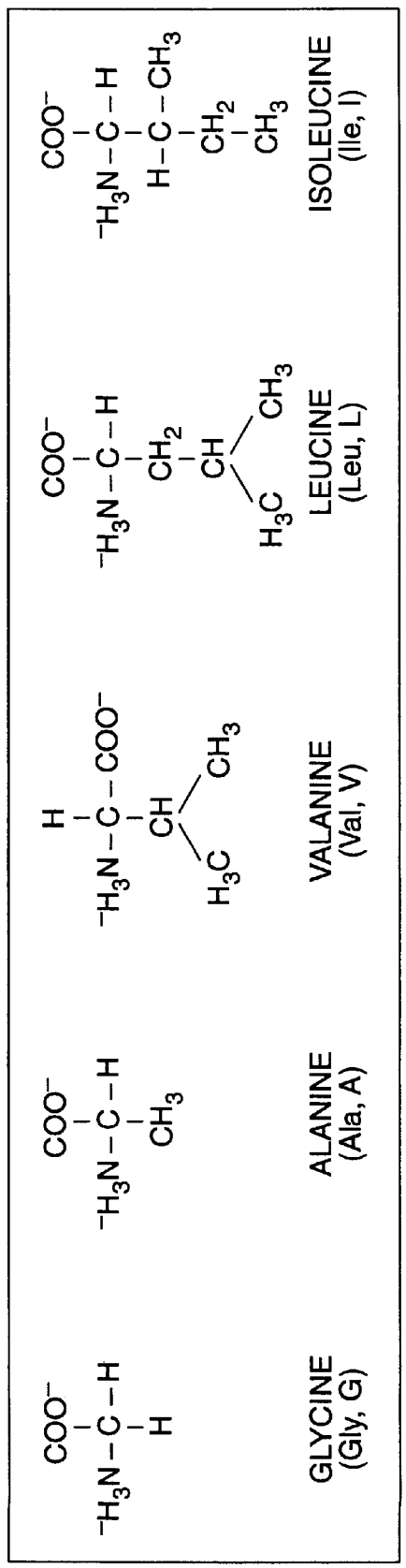

The deduced amino acid sequence of 34 antibody-positive positive clones is shown in FIG. 8. As above, only differences from the starting sequence are shown. The black dots on the right-hand side of the Figure indicate the staining category for each of the clones (°°°—intense; °°—average; °—faint). The data (summarized at the bottom of FIG. 8) indicate that the 6 amino terminal amino acids and the single carboxy terminal amino acid accept quite a number of amino acid substitutions and still bind the antibody. However amino acids in positions 7 to 12 show much less variation—in fact, an arginine at position 7 was found in 33/34 positive clones examined. The overall sequence analysis is summarized in FIG. 9. Position 8 can vary significantly but tends to be polar; position 9 is of an aromatic character (tyrosine, phenylalanine, or histidine); position 10 can vary but tends to be a polar amino acid; and the last two positions are nearly always hydrophobic. Western analysis of the induced proteins showed that the intensity of the signal on the Western blot matched the intensity of the signal in the colony lifts.

EXAMPLE 3

Construction of a Random Peptide Library with a Dodecamer Random Peptide Sequence This example illustrates how the methods and reagents of the invention can be used to generate random peptide diversity and to find peptides with affinity for a specific receptor from the diverse peptides generated.

To construct the library, BamHI-HindIII-digested plasmid pMalCΔNde was ligated to a synthetic double-stranded nucleic acid composed of single-stranded oligonucleotides ON-288, ON-272, and ON-273. These oligonucleotides are shown below in duplex form; the lower case letters in the sequence shown for oligonucleotide ON-271 indicate positions at which misincorporation was designed to occur.

```
ON-288 5'-GATCCATCGAGGGTCGTNNKNNKNNKNNKNNKNNKNNKNNKNNKNNK- (SEQ ID NO 13)

ON-272     3'-GTAGCTCCCAGCA-5'

ON-288 -NNKNNKTAAGGAGCACTGCA-3'

ON-273     3'-ATTCCTCGTGACGTTCGA-5'
```

Oligonucleotides ON-288 (0.33 μg), ON-272 (0.06 μg), and ON-273 (0.05 μg) and the BamHI-HindIII-digested plasmid pMalCΔNde (3 μg) were ligated together, and the ligated DNA was used to transform E. coli. The transformants were plated either directly on agar plates (e.g. 1.5% bactoagar in LB medium) or onto nitrocellulose filter discs (e.g. Biorad 0.45 mm pore nitrocellulose) placed on agar plates, and then incubated at 30° C. for ~16 hours, resulting in colonies with a diameter of ~0.1–0.5 mm. When this library was screened with anti-dynorphin B antibody, a number of antibody binding clones were observed.

The same library was made using oligonucleotide ON-327 in place of oligonucleotides ON-272 and ON-273 in the ligation reaction. The ON-327/ON-288 duplex is shown below.

```
ON-288 5'-GATCCATCGAGGGTCGTNNKNNKNNKNNKNNKNNKNNKNNKNNKNNK-

ON-327     3'-GTAGCTCCCAGCAIIIIIIIIIIIIIIIIIIIIIIIIIIIIIIII- (SEQ ID NO 14)

ON-288 -NNKNNKTAAGGAGCACTGCA-3'

ON-327 -IIIIIIATTCCTCGTGACGTTCGA-5'
```

In the sequence shown, I is inosine.

EXAMPLE 4
Construction of an ADR1 Misincorporation Library

The yeast ADR1 gene product is a DNA binding protein that regulates transcription of the yeast ADH gene by binding to a specific nucleic acid sequence near the ADH gene on the yeast genome. The DNA binding region of the ADR1 gene product is formed by two "zinc fingers," each formed by a sequence of amino acids that interacts with a zinc molecule. Random peptide libraries can be constructed using a scaffolding structure supplied by one or both of the ADR1 zinc fingers. These libraries can be screened for the presence of peptides that bind the ADR1 binding site on the yeast genome with greater affinity than ADR1; for the presence of peptides that bind to nucleic acid sequences other than the ADR1 binding site; and for the presence of peptides that bind metals other than zinc (see Schiff et al., June 1988, *Proc. Natl. Acad. Sci. USA* 85:4195–4199, and Makowski et al., 1991, *Biol. Trace Elem. Res.* 29:93–109, each of which is incorporated herein by reference). This example also illustrates how the methods and reagents of the invention can be used to generate random peptide diversity around the ADR1 scaffolding structure.

In a first embodiment, the random peptide and scaffolding structure take the form $X_{0-5}(F \text{ or } Y)X_1CX_{2-4}CX_3FX_5LX_{3-5}HX_{4-6}$, where X is any amino acid, the numerical subscript indicates the number of amino acids possible at the indicated location, F is phenylalanine, Y is tyrosine, C is cysteine, L is leucine, and H is histidine. This motif encodes a single zinc finger. To construct this single zinc finger library, BamHI-HindIII-digested plasmid pMalCΔNde was ligated to a synthetic double-stranded nucleic acid composed of single-stranded stranded oligonucleotides ON-375, ON-272, and ON-273. These oligonucleotides are shown below in duplex form; the lower case letters in the sequence shown for oligonucleotide ON-375 indicate positions at which misincorporation was designed to occur at a ratio of 62.5/12.5/12.5/12.5.

```
ON-375 5'-GATCCATCGAGGGTCGTagcTTCgtgTGCgaagtgTGCacccgcgcg- (SEQ ID NO 15)

ON-272       3'-GTAGCTCCCAGCA-5'

ON-375 -TTCgcgcgccaggaacatCTGaaacgcCATtatcgcagcCATaccaacg-

ON-375 -aaaaaTAAGGAGCACTGCA-3'

ON-273       3'-ATTCCTCGTGACGTTCGA-5'
```

Oligonucleotides ON-375, ON-272, and ON-273 and the BamHI-HindIII-digested plasmid pMalCΔNde were ligated together, and the ligated DNA was used to transform *E. coli*.

As a positive control, the ADR1 zinc finger was cloned into plasmid pMalcΔNde by a similar process, except that oligonucleotide ON-377 was used in place of ON-375 in the ligation. The structure of ON-377 is shown below:

```
5'-GATCCATCGAGGGTCGTAGCTTCGTGTGCGAAGTGTGCACCCGCGCG- (SEQ ID NO 16)

-TTCGCGCGCCAGGAACATCTGAAACGCCATTATCGCAGCCATACCAA-

-CGAAAAATAAGGAGCACTGCA-3'
```

In a second embodiment, the random peptide and scaffolding structure take the form: $X_{0-5}(F \text{ or } Y)X_1CX_{2-4}CX_3FX_5LX_2HX_{3-5}HX_5(F \text{ or } Y)X_1CX_{2-4}CX_3FX_5LX_2HX_{3-5}HX_{4-6}$. This motif encodes two zinc fingers, and a misincorporation library with this motif was constructed by inserting a duplex nucleic acid composed of oligonucleotides ON-378 and ON-379 into BamHI-HindIII-digested plasmid pMalCΔNde. The structure of the duplex is shown below:

```
ON-378 5-CGCGGATCCATCGAGGGTCGTagcTWCgtgTGCgaagtgTGCacccgc- (SEQ ID NO 17)

ON-378 -gcgTTCgcgcgccaggaacatCTGaaacgcCATtatcgcagcCATacca-

ON-378 -acgaaaaaCCGTWTccgTGCGGTCTGTGC-3'

ON-379        3'-GGCAWAggcACGCCAGACGCGgttgcgacgAAGtgggcggc- (SEQ ID NO 18)

ON-379 -gctagacGACtaggcgGTAcgcctgttttagGTAtcgccattggacATT-

ON-379 -TTCGAAGGGC-5'
```

In the depiction of the duplex, lower case letters indicate the misincorporated nucleotides; the misincorporation frequency was 62.5/12.5/12.5/12.5, and W is a 50/50 mixture of A and T. To form the duplex that was ligated with the digested plasmid, oligonucleotides ON-378 and ON-379 were annealed together, treated with Sequenase™ 2.0 (version 1.0 would also be suitable, U.S. Biochemicals) to "fill in" the single-stranded regions of the duplex, and digested with restriction enzymes BamHI and HindIII.

In a third embodiment, the random peptide and scaffolding structure take the form: $X_{0-25}$(F or Y)$X_1CX_{2-4}CX_3FX_5LX_2HX_{3-5}HX_5$(F or Y)$X_1CX_{2-4}CX_3FX_5LX_2HX_{3-5}HX_{4-6}$. This motif encodes two zinc fingers and an additional region, the $X_{0-25}$ region, which, when present, preferably encodes an alpha-helical, amphipathic peptide. A misincorporation library with this motif was constructed by inserting a duplex nucleic acid composed of oligonucleotides ON-447, ON-448, ON-449, and ON-450 into BamHI-HindIII-digested plasmid pMalCΔNde. The duplex was prepared by first annealing oligonucleotides ON-447 and ON-448 and treating with Sequenase to fill in the single-stranded regions of the duplex. The duplex formed by annealing ON-447 to ON-448 is shown below:

the gel, digested with restriction enzymes BamHI and HindIII, and ligated with BamHI-HindIII-digested plasmid pMalCΔNde.

EXAMPLE 5

Construction of an ADR1b Random Peptide Library

This example illustrates how the methods and reagents of the invention can be used to generate a random peptide library with a single zinc finger motif scaffolding structure and to find peptides with affinity for a specific receptor from the diverse peptides generated by the library.

To construct the library, BamHI-HindIII-digested plasmid pMalCΔNde was ligated to a synthetic double-stranded nucleic acid composed of single-stranded oligonucleotides ON-376, ON-272, and ON-273. These oligonucleotides are shown below in duplex form; the lower case letters in the sequence shown for oligonucleotide ON-375 indicate positions at which misincorporation was designed to occur at a ratio of 62.5/12.5/12.5/12.5.

```
ON-447 5'-CGCGGATCCATCGAGGGTCGTaaacagctggataaactgccggaaaa- (SEQ ID NO 19)

ON-447 -cctgcgcctgaacggccggaccCCGAGCGGCAAGCTG-3'

ON-488                      3'-GGCTCGCCGTTCGACgcatcgAWGcac- (SEQ ID NI 20)

ON-448 -ACGcttcacACGtGAGCCCGCAAGCGCGCG-5'
```

Oligonucleotides ON-449 and ON-450 were treated in a similar fashion, by annealing and then filling in with Sequenase; the duplex formed by annealing ON-449 and ON-450 is shown below:

```
ON-449 5'-TGCGAAGTGTGCACTCGGGcgTTCgcgcgccaggaacatCTGaaacg- (SEQ ID NO 21)

ON-449 -cCATtatcgcagcCATaccaacgaaaaaCCGTWTCcGTGCGGTCTGTGC-
       3'

ON-450                          3'-GGCAWAGgCACGCCAGACACG- (SEQ ID NO 22)

ON-450 -ttggcgacgAAGtgggcggcgctagacGACtaggcgGTAcgcgtctttt-

ON-450 -agGTAtcgccattggacccaATTTTCGAAGGGCC-5'
```

In the depiction of the duplexes, lower case letters indicate the misincorporated nucleotides; the misincorporation frequency was 70/10/10/10.

After each of the duplexes above were annealed and filled in with Sequenase, each duplex was digested with restriction enzyme AvaI, and the digested DNA was mixed together and ligated. The ligated DNA was separated on an acrylamide gel, and the desired fragment (composed and derived of, in order, ON-447/ON-448/ON-449/ON-450) was isolated from

```
ON-376 5'-GATCCATCGAGGGTCGTNNKTTCNNKTGCNNKNNKTGCNNKNNKNNK- (SEQ ID NO 23)

ON-272     3'-GTAGCTCCCAGCA-5'

ON-376 -TTCNNKNNKNNKNNKNNKCTGNNKNNKCATNNKNNKNNKCATNNKNNKN-

ON-376 -NKNNKTAAGGAGCACTGCA-3'

ON-273     3'-ATTCCTCGTGACGTTCGA-5'
```

Oligonucleotides ON-376, ON-272, and ON-273 and the BamHI-HindIII-digested plasmid pMalCΔNde were ligated together, and the ligated DNA was used to transform E. coli.

EXAMPLE 6
Construction of an Zinc Binding Motif Random Peptide Library

A number of different motifs can be used for metal coordination of the random peptide (see Vallee et al., February 1991, Proc. Natl. Acad. Sci. USA 88:999–1003, and Miller et al., March 1992, Proc. Natl. Acad. Sci. USA 89:2032–2035, each of which is incorporated herein by reference). For purposes of the present invention, these motifs include the following: $CX_2CX_4HX_4C$, $CX_2Cx_{16}Cx_2C$, $CX_2CX_6CX_6CX_2CX_6C$, $X_2CX_2CX_4HX_4CX_2$, $CX_2CX_6HX_2H$, $CX_2CX_{12-14}HX_2H$, $CX_2CX_{13}CX_2CX_{15}CX_5CX_8C$, $X_2CX_2CX_6HX_2HX_2$, and $X_3CX_2CX_6CX_6CX_2CX_6CX_3$. X is any amino acid. This example illustrates how the methods and reagents of the invention can be used to generate random peptide diversity using the $X_2CX_2CX_4HX_4CX_2$ motif and to find peptides with affinity for a specific receptor from the diverse peptides generated.

To construct the library, BamHI-HindIII-digested plasmid pMalCΔNde was ligated to a synthetic double-stranded nucleic acid composed of single-stranded oligonucleotides ON-384, ON-272, and ON-273. These oligonucleotides are shown below in duplex form.

```
ON-384  5'-GATCCATCGAGGGTCGT(NNK)2TGC(NNK)2TGC(NNK)4-  (SEQ ID NO 24)

ON-272           3'-GTAGCTCCCAGCA-5'

ON-384  -CAT(NNK)4TGCNNKNNKTAAGGAGCACTGCA-3'

ON-273                    3'-ATTCCTCGTGACGTTCGA-5'
```

Oligonucleotides ON-384, ON-272, and ON-273 and the BamHI-HindIII-digested plasmid pMalCΔNde were ligated together, and the ligated DNA was used to transform E. coli.

A zinc binding peptide library is prepared as generally described above, by synthesizing oligonucleotides containing degenerate codons of the NNK (or NNS) motif interspersed at particular locations with codons specifying the zinc-coordinating ligands cysteine (whose codons are TGT or TGC) and histidine (whose codons are CAT and CAC). In addition to zinc, this type of peptide framework scaffold may also bind similar metal atoms such as (but not limited to) cadmium, nickel, or iron.

Specific zinc (or other metal coordinating) frameworks can be the so-called zinc box, or CCHC motif, (see for example Berg (J. Biol. Chem. 265:6513–6516 (1990)) which can consist of X-X-C-X-X-C-X-X-X-X-H-X-X-X-X-C-X-X, where X is NNK (or NNS), C is a cysteine codon, and H is a histidine codon. A subset or peptides having this structure can successfully tetrahedrally coordinate a zinc (or cadmium, or nickel, etc.) atom and can result in a conformationally constrained peptide for presentation to receptors (or antibodies or enzymes) as candidate binding agents.

As noted above, specific zinc (or other metal coordinating) frameworks can also be the so-called zinc finger motif. In the example given, the zinc finger motif is patterned after that of the ADR1 protein of the bakers yeast Saccharomyces cereviseae (see, for example, Thukral et al. (Molec. Cell. Biol. 9:2360–2369 (1989) and references therein). This two-finger motif scaffold is specified by the framework X-X-a-X-C-X-X-C-X-X-X-F-X-X-X-X-X-L-X-X-H-X-X-X-H-X-X-X-X-X-a-X-C-X-X-C-X-X-X-F-X-X-X-X-X-L-X-X-H-X-X-X-X-H-X-X-X-X where X is NNK (or NNS), C is a cysteine codon (TGT or TGC), H is a histidine codon (CAC or CAT), a is an aromatic amino acid codon, i.e. tyrosine TAT or TAC or phenelyalanine (TTT or TTC), L is a leucine codon (TTA, TTG, CTA, CTC, CTG, or CTT) and F is a phenylalanine codon (TTT or TTC). In the zinc finger peptide scaffold, amino acid residues in adition to the metal-coordinating cysteines and histidines are also conserved to increase the likelihood of successful peptide folding—namely the hydrophobic amino acid leucine at the positions noted and the aromatic amino acids tyrosine or phenylalanine at the positions noted. A subset of peptides in the libraries having this structure can successfully tetrahedrally coordinate a zinc (or cadmium, or nickel, etc. atom), or two metal atoms (one for each finger) and conformationally constrain the peptide for presentation to receptors (or antibodies or enzymes) as a candidate binding agent.

A similar stategy can be employed to build a metal-coordinating peptide library around the so-called zinc-cluster (see Vallee et al., 1991, Proc. Natl. Acad. Sci. USA 88: 999–1003, incorporated herein by reference). The use of appropriate metal chelation agents and metal ion solutions can allow the replacement of one metal in the peptides of the library by a similar but different metal (e.g. replace zinc by cadmium). One can then change the receptor (an antibody, enzyme, or other receptor) binding properties of individual members of the library by the choice of the metal used to induce the conformational constraint.

EXAMPLE 7
Construction of a Beta Turn Motif Random Peptide Library

This example illustrates the use of a beta turn motif in a random peptide library of the invention. The beta turn motif is represented by $X_5HX_2HX_5$, where X is a random amino acid, and H is histidine. To construct the library, BamHI-HindIII-digested plasmid pMalCΔNde is ligated to a synthetic double-stranded nucleic acid composed of single-stranded oligonucleotides ON-663, ON-272, and ON-273.

These oligonucleotides are shown below in duplex form.

```
ON-663  5'-GATCCATCGAGGGTCGTNNKNNKNNKNNKNNKCACNNKNNKCAC-  (SEQ ID NO 25)

ON-272           3'-GTAGCTCCCAGCA-5'

ON-663  -NNKNNKNNKNNKNNKTAAGGAGCACTGCA-3'

ON-273                    3'-ATTCCTCGTGACGTTCGA-5'
```

Oligonucleotides ON-663, ON-272, and ON-273 and the BamHI-HindIII-digested plasmid pMalCΔNde are ligated together, and the ligated DNA is used to transform *E. coli* to construct the library.

EXAMPLE 8

Construction of an Alpha Helix Motif Random Peptide Library

This example illustrates the use of an alpha helix motif in a random peptide library of the invention. The alpha helix motif is represented by A4X5HX3HX5A4, Where A is alanine, X is a random amino acid, and H is histidine. To construct the library, BamHI-HindIII-digested plasmid pMalCΔNde is ligated to a synthetic double-stranded nucleic acid composed of single-stranded oligonucleotides ON-664, ON-272, and ON-273. These oligonucleotides are shown below in duplex form.

```
ON-664  5'-GATCCATCGAGGGTCGTGCAGCAGCAGCANNKNNKNNKNNKNNKCAC- (SEQ ID NO 26)

ON-272            3'-GTAGCTCCCAGCA-5'

ON-664 -(NNK)3CAC(NNK)5GCAGCAGCAGCATAAGGAGCACTGCA-3'

ON-273                              3'-ATTCCTCGTGACGTTCGA-5'
```

Oligonucleotides ON-664, ON-272, and ON-273 and the BamHI-HindIII-digested plasmid pMalCΔNde are ligated together, and the ligated DNA is used to transform *E. coli* to construct the library.

Although the foregoing invention has been described in some detail by way of illustration and example for purposes of clarity of understanding, it will be apparent that certain changes and modifications may be practiced within the scope of the appended claims.

---

I claim:

1. A method of generating a peptide library comprising the steps of:

(a) transforming host cells with a set of recombinant DNA vectors, each member of which encodes a different tripartite fusion protein consisting essentially of a carrier protein, a peptide, and a proteolytic cleavage site between said carrier protein and said peptide, such that at least 1000 and up to about $10^8$ different transformants are formed, wherein said different members differ from one another with respect to the peptide encoded; and (b) culturing said host cells transformed in step (a) under conditions suitable for expression of the fusion protein.

2. The method of claim 1, wherein said host cell is *E. coli*, said vector is a plasmid, said carrier protein is selected from the group consisting of maltose binding protein, streptavidin, $His_n$ where n is at least 3, ubiquitin, cellulose binding protein, and glutathione-S-transferase, and said proteolytic cleavage site is selected from the group consisting of a site for Factor Xa cleavage, a site for enterokinase cleavage, and a site for collagenase cleavage.

3. The method of claim 2, wherein said carrier protein is the maltose binding protein and said proteolytic cleavage site is a site for Factor Xa cleavage.

4. The method of claim 3, wherein said plasmid further encodes a signal peptide that directs secretion of the tripartite fusion protein into the periplasm of said host cell.

5. The method of claim 3, wherein said peptide is five to seventy-five amino acid residues in length.

6. The method of claim 5, wherein said peptide comprises amino acid residues that introduce conformational constraints on the peptide.

7. The method of claim 6, wherein said peptide assumes a conformation characteristic of a conformation selected from the group consisting of a zinc finger, leucine zipper, cysteine crosslinking via disulphide bridge formation, beta turn, and alpha helix.

8. The method of claim 1, wherein said peptide library is a secondary library, and said peptide of said tripartite fusion protein is a variation of a lead peptide sequence.

\* \* \* \* \*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ile Glu Gly Arg
1

(2) INFORMATION FOR SEQ ID NO:2:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Asp Asp Asp Lys
1

(2) INFORMATION FOR SEQ ID NO:3:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

Pro Val Gly Pro
1

(2) INFORMATION FOR SEQ ID NO:4:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

Tyr Gly Gly Phe Leu
1               5

(2) INFORMATION FOR SEQ ID NO:5:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:5:

Tyr Gly Gly Phe Leu Arg Arg Gln Phe Lys Val Val Thr
1               5                   10

(2) INFORMATION FOR SEQ ID NO:6:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:6:

Gly Lys Arg Xaa
1

(2) INFORMATION FOR SEQ ID NO:7:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:7:

GATCCATCGA GGGTCGTTAC GGTGGTTTCC TGCGTCGTCA GTTCAAAGTT GTTACCTAAA      60

(2) INFORMATION FOR SEQ ID NO:8:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

AGCTTTTAGG TAACAACGTT GAACTGACGA CGCAGGAAAC CACCGTAACG ACCCTCGATG    60

(2) INFORMATION FOR SEQ ID NO:9:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

GATCCATCGA GGGTCGTTAC GGTGGTTTCC TGCGTCGTCA GTTCAAAGTT GTTACCTAAG    60

GAGCACTGCA                                                          70

(2) INFORMATION FOR SEQ ID NO:10:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

ACGACCCTCG ATG                                                      13

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

AGCTTGCAGT GCTCCTTA                                                 18

(2) INFORMATION FOR SEQ ID NO:12:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO:12:

GGTCGTCAGA CTGTGCATGA AGCC                                          24

(2) INFORMATION FOR SEQ ID NO:13:

(i) SEQUENCE CHARACTERISTICS:
            (A) LENGTH: 67 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GATCCATCGA GGGTCGTNNK NNKNNKNNKN NKNNKNNKNN KNNKNNKNNK NNKTAAGGAG    60

CACTGCA                                                             67

(2) INFORMATION FOR SEQ ID NO:14:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 18...54
        (D) OTHER INFORMATION: /note= N is inosine (xi) SEQUENCE DESCRIPTION: SEQ ID NO:14:

AGCTTGCAGT GCTCCTTANN NNNNNNNNNN NNNNNNNNNN NNNNNNNNNN NNNNACGACC    60

CTCGATG                                                             67

(2) INFORMATION FOR SEQ ID NO:15:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GATCCATCGA GGGTCGTAGC TTCGTGTGCG AAGTGTGCAC CCGCGCGTTC GCGCGCCAGG    60

AACATCTGAA ACGCCATTAT CGCAGCCATA CCAACGAAAA ATAAGGAGCA CTGCA        115

(2) INFORMATION FOR SEQ ID NO:16:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GATCCATCGA GGGTCGTAGC TTCGTGTGCG AAGTGTGCAC CCGCGCGTTC GCGCGCCAGG    60

AACATCTGAA ACGCCATTAT CGCAGCCATA CCAACGAAAA ATAAGGAGCA CTGCA        115

(2) INFORMATION FOR SEQ ID NO:17:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:17:

CGCGGATCCA TCGAGGGTCG TAGCTWCGTG TGCGAAGTGT GCACCCGCGC GTTCGCGCGC      60

CAGGAACATC TGAAACGCCA TTATCGCAGC CATACCAACG AAAAACCGTW TCCGTGCGGT     120

CTGTGC                                                               126

(2) INFORMATION FOR SEQ ID NO:18:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGGGAAGCTT TTACAGGTTA CCGCTATGGA TTTTGTCCGC ATGGCGGATC AGCAGATCGC      60

GGCGGGTGAA GCAGCGTTGG CGCAGACCGC ACGGAWACGG                           100

(2) INFORMATION FOR SEQ ID NO:19:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CGCGGATCCA TCGAGGGTCG TAAACAGCTG GATAAACTGC CGGAAAACCT GCGCCTGAAC      60

GGCCGGACCC CGAGCGGCAA GCTG                                            84

(2) INFORMATION FOR SEQ ID NO:20:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCGCGCGAAC GCCCGAGTGC ACACTTCGCA CACGWAGCTA CGCAGCTTGC CGCTCGG         57

(2) INFORMATION FOR SEQ ID NO:21:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TGCGAAGTGT GCACTCGGGC GTTCGCGCGC CAGGAACATC TGAAACGCCA TTATCGCAGC      60

CATACCAACG AAAAACCGTW TCCGTGCGGT CTGTGC                                96

(2) INFORMATION FOR SEQ ID NO:22:

(i) SEQUENCE CHARACTERISTICS:
        (A) LENGTH: 104 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

CCGGGAAGCT TTTAACCCAG GTTACCGCTA TGGATTTTCT GCGCATGGCG GATCAGCAGA      60

TCGCGGCGGG TGAAGCAGCG GTTGCACAGA CCGCACGGAW ACGG                     104

(2) INFORMATION FOR SEQ ID NO:23:

(i) SEQUENCE CHARACTERISTICS:
            (A) LENGTH: 115 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

GATCCATCGA GGGTCGTNNK TTCNNKTGCN NKNNKTGCNN KNNKNNKTTC NNKNNKNNKN      60

NKNNKCTGNN KNNKCATNNK NNKNNKCATN NKNNKNNKNN KTAAGGAGCA CTGCA          115

(2) INFORMATION FOR SEQ ID NO:24:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:24:

GATCCATCGA GGGTCGTNNK NNKTGCNNKN NKTGCNNKNN KNNKNNKCAT NNKNNKNNKN      60

NKTGCNNKNN KTAAGGAGCA CTGCA                                           85

(2) INFORMATION FOR SEQ ID NO:25:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

NNKNNKNNKN NKNNKTAAGG AGCACTGCA                                       29

(2) INFORMATION FOR SEQ ID NO:26:

(i) SEQUENCE CHARACTERISTICS:
            (A) LENGTH: 100 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

GATCCATCGA GGGTCGTGCA GCAGCAGCAN NKNNKNNKNN KNNKCACNNK NNKNNKCACN      60

NKNNKNNKNN KNNKGCAGCA GCAGCATAAG GAGCACTGCA                          100